(12) United States Patent
Takamine et al.

(10) Patent No.: US 9,109,266 B2
(45) Date of Patent: Aug. 18, 2015

(54) PROCESS OF PRODUCING SUGAR COMPOSITION COMPRISING D-PSICOSE AND D-ALLOSE VIA STRONG ALKALINE ISOMERIZATION OF D-GLUCOSE/D-FRUCTOSE OR ALKALINE PRE-TREATMENT OF D-GLUCOSE/D-FRUCTOSE FOLLOWED BY ISOMERIZATION IN THE PRESENCE OF A BASIC ION EXCHANGE RESIN

(75) Inventors: Satoshi Takamine, Itami (JP); Tetsuo Iida, Itami (JP); Kazuhiro Okuma, Itami (JP); Tsuyoshi Shimonishi, Kita-gun (JP); Ken Izumori, Kita-gun (JP); Tatsuhiro Matsuo, Kita-gun (JP)

(73) Assignees: MATSUTANI CHEMICAL INDUSTRY CO., LTD., Itami-shi (JP); IZUMORING CO., LTD., Kita-gun (JP); NATIONAL UNIVERSITY CORPORATION KAGAWA UNIVERSITY, Takamatsu-shi (JP)

( * ) Notice: Subject to any disclaimer, the term of this patent is extended or adjusted under 35 U.S.C. 154(b) by 145 days.

(21) Appl. No.: 13/262,558

(22) PCT Filed: Mar. 26, 2010

(86) PCT No.: PCT/JP2010/055336
§ 371 (c)(1),
(2), (4) Date: Dec. 15, 2011

(87) PCT Pub. No.: WO2010/113785
PCT Pub. Date: Oct. 7, 2010

(65) Prior Publication Data
US 2012/0094940 A1   Apr. 19, 2012

(30) Foreign Application Priority Data

Mar. 30, 2009 (JP) .................................. 2009-81976

(51) Int. Cl.
| | | |
|---|---|---|
| C13K 13/00 | (2006.01) |
| A23L 1/236 | (2006.01) |
| A23L 2/60 | (2006.01) |
| A61K 8/60 | (2006.01) |
| A61K 31/7004 | (2006.01) |
| A61K 47/26 | (2006.01) |
| A61Q 19/00 | (2006.01) |
| C07H 3/02 | (2006.01) |

(52) U.S. Cl.
CPC ............. *C13K 13/007* (2013.01); *A23L 1/2363* (2013.01); *A23L 2/60* (2013.01); *A61K 8/60* (2013.01); *A61K 31/7004* (2013.01); *A61K 47/26* (2013.01); *A61Q 19/00* (2013.01); *C07H 3/02* (2013.01)

(58) Field of Classification Search
None
See application file for complete search history.

(56) References Cited

U.S. PATENT DOCUMENTS

| 3,285,776 A * | 11/1966 | Scallet et al. ................... 127/30 |
| 5,433,793 A * | 7/1995 | Herber et al. ................. 127/46.1 |
| 2009/0068710 A1 * | 3/2009 | Izumori et al. .................. 435/94 |

FOREIGN PATENT DOCUMENTS

| EP | 109203 A1 * | 5/1984 | ............... C07H 3/02 |
| EP | 302970 A1 * | 2/1989 | ............... C07H 3/02 |

OTHER PUBLICATIONS

Beveridge, Davis and Morris. The preparation of decagram quantities of d-psicose by the isomerization of d-fructose, and separation of the products on a calcium-ion cation-exchange resin. Carbohydrate Research, 101, 2, 1982, pp. 348-349.*

Doner, L. Isomerization OP D-Fructose by Base: Liquid-Chromatographic Evaluation and the Isolation OP D-Psicose. Carbohydrate Research, 70, 2, 1979, pp. 209-216.*

Wolfrom, M. L., & Schumacher, J. N. (1955). The Action of Alkali on D-Fructose1. Journal of the American Chemical Society, 77(12), 3318-3323.*

* cited by examiner

*Primary Examiner* — Shaojia Anna Jiang
*Assistant Examiner* — Dale R Miller
(74) *Attorney, Agent, or Firm* — Westerman, Hattori, Daniels & Adrian, LLP

(57) ABSTRACT

Problems
Development of a process of producing inexpensive and safe hexose and compositions of the same.
Means for Resolution
A process of producing a sugar composition comprising a definite amount of an target hexose, comprising treating a starting liquid sugar material comprising a starting sugar material hexose or a mixture comprising hexose in a system in the presence of one or more types selected from the group consisting of basic ion exchange resins, alkalis and calcium salts to initiate an isomerization reaction as an equilibrium reaction to transform the starting sugar material hexose to the target hexose to prepare a sugar mixture comprising a definite amount of the target hexose and having a sugar constitution different from that of the starting sugar material, and hexose compositions containing D-allose and D-psicose and the use of the hexose compositions.

8 Claims, 6 Drawing Sheets

PROCESS OF PRODUCING SUGAR COMPOSITION COMPRISING D-PSICOSE AND D-ALLOSE VIA STRONG ALKALINE ISOMERIZATION OF D-GLUCOSE/D-FRUCTOSE OR ALKALINE PRE-TREATMENT OF D-GLUCOSE/D-FRUCTOSE FOLLOWED BY ISOMERIZATION IN THE PRESENCE OF A BASIC ION EXCHANGE RESIN

TECHNICAL FIELD

The present invention relates to a process of producing a sugar composition comprising a definite amount of a target hexose from a starting liquid sugar material and having a sugar constitution different from that of a starting sugar material, and the use of the produced sugar composition. Additionally, the invention relates to a process of producing an isomerized sugar syrup of a transformation type comprising psicose and allose, from an "isomerized sugar syrup" comprising glucose and fructose as the main components, which is broadly defined as a sugar mixture; an isomerized sugar syrup of a transformation type, comprising definite amount of psicose and allose produced; and the use thereof.

[Definition of Isomerized Sugar]

Generally, a sugar mixture of glucose and fructose at a specific constitution ratio is designated as isomerized sugar syrup. In accordance with the invention, however, the term isomerized sugar syrup is broadly defined by a sugar mixture comprising glucose and fructose as the main components.

BACKGROUND OF THE INVENTION

A representative process of the process of producing an isomerized sugar syrup, comprising saccharifying starch to a saccharified solution and treating the saccharified solution with glucose isomerase comprises hydrolyzing starch with an enzyme to dextrin and hydrolyzing then dextrin with a different enzyme to a glucose solution, namely saccharified solution. The isomerization reaction of glucose with glucose isomerase to fructose is an equilibrium reaction, where the ratio of glucose and fructose in the isomerized sugar syrup is generally about 58:42. So as to overcome poor sweetness, further, purified fructose may sometimes be added. In that case, the final ratio of glucose and fructose is generally about 45:55. From the standpoint of low production cost, the isomerized sugar syrup is widely used as a sweetener in soft drinks and other drinks. In USA, the isomerized sugar syrup is consumed up to 8,000,000 tons or more yearly.

Attention has been focused recently on rare sugars because rare sugars have various physiological effects. Therefore, research works have been done intensively. For wide industrial application, furthermore, efficient production of these rare sugars is essential.

One of rare sugars, namely D-psicose is produced at a yield of 20 to 25 from D-fructose by allowing D-ketohexose.3-epimerase (patent reference 1) to react with D-fructose. A certain report tells that in case that D-psicose.3-epimerase (non-patent reference 1) is used, still furthermore, D-psicose is produced at a yield of about 40% and that in case that boric acid is used in combination, D-psicose is produced at about 60%. In case of industrially producing rare sugars at amass scale using the enzymes, the safety profiles of the enzymes should be validated first; and then, problems regarding bacterial cell culture and purification as an enzyme source and individual production steps of absorbents and the like should be overcome one after another.

PRIOR TECHNICAL REFERENCES

Patent References

Patent reference 1: JP-A-Hei 6-125776
Patent reference 2: JP-A-2001-352936
Patent reference 3: EP 0 109 203 A1
Patent reference 4: PCT/JP2008/001240
Patent reference 5: JP-A-2001-354690
Patent reference 6: JP-A-2006-153591
Patent reference 7: JP-A-2007-091696

Non-Patent References

Non-patent reference 1: Appl. Environ. Microbiol., 2008, 74(10), 3008-13.
Non-patent reference 2: Carbohydr. Res., 1987, 169, 13-21.
Non-patent reference 3: J. Am. Chem. Soc. 1955, 77(12), 3323-5
Non-patent reference 4: Seibutu Kogaku Kaishi (Journal of Bioindustry Association), 2008, 86(9), 427-42.
Non-patent reference 5: Metabolism, 2010, 59, 206-14.
Non-patent reference 6: J. Agric. Food Chem., 2003, 51, 1894-6.
Non-patent reference 7: J. Clin. Biochem. Nutr., 2009, 45, 202-6.
Non-patent reference 8: J. Oleo. Sci., 2004, 53(9), 453-60.
Non-patent reference 9: Rare Sugar Congress 2008 in Kagawa, Poster Presentation, Acute and Chronic Toxicity of D-allose in Rats.
Non-patent reference 10: Biochimica et Biophysica Acta. 2001, 1528, 116-26.
Non-patent reference 11: Biosci. Biotechnol. Biochem., 2006, 70(9), 2081-5.

DISCLOSURE OF THE INVENTION

Problems that the Invention is to Solve

Since the 1800s, alternatively, an isomerization reaction between aldose and ketose through enediol has been known, which is called the Lobry de Bruyn and Alberda van Ekenstein transformation. By the isomerization reaction, a certain hexose can be isomerized to another hexose by leaving the certain hexose under alkali conditions. By using the reaction, hexose may be isomerized (non-patent reference 2). So as to obtain an isomerized material at a physiologically active concentration, there are problems such as the need of reaction times unsatisfactory for actual industrial production efficiency and significant coloring of the resulting product via caramel preparation, causing difficulty in subsequent purification. In case of mass-scale production via batch-wise reaction, problems emerge regarding equipment scale and multiple steps. Hence, actual industrial application of the reaction is very hard.

Although sweetness enhancers comprising mannose are proposed as sweetness enhancers, together with application methods thereof, regarding the use of the physiological actions of the composition obtained by the method described above (patent reference 2), the sweetness enhancers and the application methods are never actually practiced. Consequently, the application of the composition as a sweetener, an anti-obesity agent, an appetite suppressant, an amelioration agent of insulin resistance, and a low-calories sweetener has never borne any fruitful results.

It has been concerned recently that sugar materials (assimilable sugar) representatively including isomerized sugar syrup and sucrose cause diabetes mellitus and obesity. Therefore, sweeteners with excellent sweetness and without occurrence of such diseases on the basis of these assimilable sugars are desirably introduced on markets. In accordance with the invention, a composition overcoming such adverse actions or drawbacks of these assimilable sugars, particularly isomerized sugar syrup, as described above, was investigated.

With respect to the reaction, furthermore, the non-patent reference 3 describes reactions to generate sorbose, mannose and fructose from glucose, using ion exchange resins. However, the reactions are, unlike the invention, do not enable a continuous reaction by packing resins in a chromatographic column and then passing a solution through the column together with an alkali so that the productivity can be improved. Unlike D-psicose production in accordance with the invention, furthermore, the non-patent reference 3 never reports anything about the application to the production process of D-psicose. No examination of compositions comprising D-psicose and D-allose has been made so far.

As described above, additionally, no industrially applicable production process of a rare sugar hexose has been obtained from the standpoints of efficient production and safety profile.

In view of production process, hence, it is an object of the invention to establish a production process of a rare sugar hexose with no use of enzymes, by which it is expected that [1] a production step of a needed enzyme and a reaction step with the enzyme among factors causing a great number of production steps can be omitted and [2] problems regarding safety such as enzyme leakage and contamination with bacterial cell residues can be eliminated.

It is also an object of the invention to prevent the significant browning change emerging during the application of the Lobry de Bruyn and Alberda van Ekenstein transformation (see FIG. 1) to improve the yield and the productivity. Herein, the improvement of the productivity means [3] for example that the amount of purification resins to be used for removing significantly browned substances can markedly be reduced and some of the steps can be omitted. In accordance with the invention, furthermore, it is an object to prevent the browning change by passing a solution through a column packed with ion exchange resins to prevent browning change and to improve the productivity of the objective rare sugar hexose. It is an additional object [4] to overcome a problem such that when a starting sugar material and acidic byproducts adsorb to resins, the reaction hardly progresses.

Furthermore, it is an object of the invention [5] to construct a series of industrial production plants for reactions, separations and reuse of byproducts by linking the reaction on resins to a continuous reaction, to reduce the production steps. It is also an object [6] to examine chromatographic separation conditions since these complicated reaction products are separated by chromatography. It is an object of the invention [7] to obtain an industrial system to obtain given reaction products by adding a starting sugar material to the separated product, so as to never disturb the chromatographic separation conditions.

From the standpoint of the physiological actions of a sugar composition and with attention focused on the physiological actions of a specific hexose, in accordance with the invention, it is an object to produce a sugar composition comprising a specific hexose, namely [8] to establish the use of a composition obtained by allowing a hexose to react with an alkali to define the product and the constitution ratio.

More specifically, for example, objects of the invention are to provide an industrially applicable process of producing an "isomerized sugar syrup" of a transformation type comprising psicose and allose, from an "isomerized sugar syrup" broadly defined by a sugar mixture containing glucose and fructose as the main components or from glucose and/or fructose, and to provide an isomerized sugar syrup of a transformation type comprising specific amounts of psicose and allose and having excellent physiological effects and to establish the use thereof.

It is an object of the invention to overcome the problems [1] to [8] to provide a process of producing all hexose types and the use of the obtained compositions.

Furthermore, it is an object of the invention to provide foods, pharmaceutical products or pseudo-pharmaceutical products, oral compositions and cosmetics, which contain rare sugars.

Means for Solving the Problems

So as to solve the problems, the inventor made investigations. Thus, the invention has been achieved, on the basis of the finding that a starting material hexose or a mixture thereof can be transformed to hexose of a type different from that of the starting sugar material in a system in the presence of one or more types selected from the group consisting of strongly basic ion exchange resins, alkalis and calcium salts. Among them, in particular, the ion exchange course essential for sugar manufacture works for the reaction and purification. In other words, a sugar mixture is efficiently produced via a continuous reaction in a column; at the next course, then, the sugar mixture is separated by chromatography; byproducts are added to a starting sugar material for successful efficient production, significantly. Furthermore, examination was made about the sugar constitution of sugar compositions obtained by alkali isomerization of hexose and the use thereof, including a case by means of ion exchange resins. Thus, inventions of pharmaceutical products and cosmetics have been achieved successfully.

In other words, the invention is summarized as processes of producing a sugar composition comprising a definite amount of a target hexose, as described below in (1) through (14).

(1) A process of producing a sugar composition comprising a definite amount of an target hexose, characterized by comprising treating a starting liquid sugar material which comprises hexose or a mixture thereof in the presence of at least one member selected from the group consisting of a basic ion exchange resin, an alkali and a calcium salt, and thus performing an isomerization reaction which is an equilibrium reaction for transforming the hexose as a starting sugar material into the target hexose, to thereby give a sugar mixture containing a definite amount of the target hexose and having a sugar constitution different from that of the starting sugar material.

(2) A process of producing a sugar composition according to the above (1), where the concentration of the hexose in the starting liquid sugar material is 5.0 w/w % to 100 w/w %.

(3) A process of producing a sugar composition comprising according to the above (1) or (2), where the hexose in the starting liquid sugar material is one or more hexose types selected from the group consisting of D-fructose, D-glucose, D-psicose, D-mannose, D-allose and D-altrose.

(4) A process of producing a sugar composition according to the above (3), where the hexose in the starting liquid sugar material is an isomerized sugar syrup containing D-glucose and D-fructose as the main components.

(5) A process of producing a sugar composition according to the above (4), where the hexose in the starting liquid sugar material is an isomerized sugar syrup containing D-glucose and D-fructose as the main components, and the target hexose given contains D-psicose and D-allose.

(6) A process of producing a sugar composition according to the above (5), where the isomerized sugar syrup containing D-glucose and D-fructose as the main components and the definite amount of the target hexose is 0.5 to 17.0 of D-psicose and 0.2 to 10.0% of D-allose in the sugar mixture given.

(7) A process of producing a sugar composition according to the above (1) or (2), where the hexose in the starting liquid sugar material contains one or more of the members selected from the group consisting of L-fructose, L-glucose, L-psicose, L-mannose, L-allose and L-altrose.

(8) A process of producing a sugar composition according to the above (1) or (2), where the hexose in the starting liquid sugar material is one or more of the members selected from the group consisting of D-tagatose, D-talose, D-galactose, D-sorbose, D-gulose, and D-idose.

(9) A process of producing a sugar composition comprising according to the above (1) or (2), where the hexose in the starting liquid sugar material is one or more of the members selected from the group consisting of L-tagatose, L-talose, L-galactose, L-sorbose, L-gulose, and L-idose.

(10) A process of producing a sugar composition according to anyone of the above (1) through (9), where the starting liquid sugar material is preliminarily prepared as an alkaline for being treated in a system in the presence of a basic ion exchange resin to improve the yield of the target sugar hexose.

(11) A process of producing a sugar composition according to anyone of the above (1) through (10), where the starting liquid sugar material is treated in the presence of a basic ion exchange resin, followed by passing the resulting solution through an acidic ion exchange resin and/or a mixed ion exchange resin for neutralizing and desalting.

(12) A process of producing a sugar composition according to any one of the above (1) through (11), where the concentration of an alkali in the starting liquid sugar material is 0.005 mol/l or more as the starting liquid sugar material is treated in the presence of the alkali.

(13) A process of producing a sugar composition comprising according to any one of the above (1) through (12), where the concentration of a calcium salt in the starting liquid sugar material is 0.005 mol/l or more as the starting liquid sugar material is treated in the presence of the calcium salt.

(14) A process of producing a sugar composition according to any one of the above (1) through (13), where the target hexose is separated from the sugar mixture and the resulting residue is returned as a raw material to the starting liquid sugar material.

Furthermore, the invention is summarized as the sugar-like sweetener, the food, the pharmaceutical product or pseudo-pharmaceutical product, the oral composition or the cosmetic described below in (15).

(15) A sugar-like sweetener, a food, a pharmaceutical product or pseudo-pharmaceutical product, an oral composition or a cosmetic composition, containing the sugar mixture which contains target hexose, produced by the process according to any one of the above (1) through (14), having a sugar constitution different from that of the starting sugar material.

Furthermore, the invention is summarized as the sugar composition described below in (16).

(16) sugar composition, containing 0.5 to 17.0% of D-psicose and 0.2 to 10.0% of D-allose, produced by the process according to any one of the above (1) through (6) or any one of the above (10) through (14) from an isomerized sugar syrup containing D-glucose and D-fructose as the main components or from a sugar solution comprising D-glucose and/or D-fructose as a raw material, and having a sugar constitution different from that of the starting sugar syrup or solution.

Namely, a sugar composition comprising D-psicose and D-allose and having a sugar constitution different from that of a starting sugar material, as produced by treating an isomerized sugar syrup as a sugar mixture containing D-glucose and D-fructose as the main components as starting sugar materials or a starting liquid sugar material comprising D-glucose and/or D-fructose in a system in the presence of one or more types selected from the group consisting of basic ion exchange resins, alkalis and calcium salts to initiate an isomerization reaction as an equilibrium reaction to transform D-glucose and/or D-fructose as the starting sugar materials to target D-psicose and D-allose, where the constitution comprises D-psicose at 0.5 to 17.0% of the sugar content and D-allose at 0.2 to 10.0% of the sugar content.

Still further, the invention is summarized as the anti-obesity agent, the appetite suppressant, the amelioration agent of insulin resistance, the low-calories sweetener, or the sugar-like sweetener, described below in (17).

(17) An anti-obesity agent, an appetite suppressant, an amelioration agent of insulin resistance, a low-calories sweetener, or a sugar-like sweetener containing a sugar mixture which contains 0.5 to 17.0 of D-psicose and 0.2 to 10.0% of D-allose, produced by a process according to the above (16) from an isomerized sugar syrup containing D-glucose and D-fructose as the main components or from a sugar solution comprising D-glucose and/or D-fructose as a raw material, and having a sugar constitution different from that of the starting sugar syrup or solution.

Namely, an anti-obesity agent, an appetite suppressant, an amelioration agent of insulin resistance, a low-calories sweetener, or a sugar-like sweetener, containing the sugar composition described above.

(a) an anti-obesity agent containing a sugar mixture produced from an isomerized sugar syrup as a sugar mixture comprising D-glucose and D-fructose as the main components or a starting material D-glucose and/or D-fructose by transforming D-glucose and/or D-fructose to D-psicose and D-allose to a final D-psicose content of 0.5 to 17.0% of the sugar content and a final D-allose content of 0.2 to 10.0% of the sugar content as the active components.

In case that "D-glucose and/or D-fructose" is a starting sugar material in (a) above, the following embodiments 1) to 3) are included. The same is true with (b), (c), (d) and (e) below.

1) An anti-obesity agent containing a sugar mixture produced from a starting material D-glucose, by transforming D-glucose to D-psicose and D-allose to a final D-psicose content of 0.5 to 17.0% of the sugar content and a final D-allose content of 0.2 to 10.0% of the sugar content as the active components.

2) An anti-obesity agent containing a sugar mixture produced from a starting material D-fructose, by transforming D-fructose to D-psicose and D-allose to a final D-psicose content of 0.5 to 17.0% of the sugar content and a final D-allose content of 0.2 to 10.0% of the sugar content as the active components.

3) An anti-obesity agent containing a sugar mixture produced from starting material D-glucose and D-fructose, by transforming D-glucose and D-fructose to D-psicose and D-allose to a final D-psicose content of 0.5 to 17.0% of the sugar content and a final D-allose content of 0.2 to 10.0% of the sugar content as the active components.

(b) An appetite suppressant containing a sugar mixture produced from an isomerized sugar syrup as a sugar mixture containing D-glucose and D-fructose as the main components or a starting material D-glucose and/or D-fructose, by transforming D-glucose and/or D-fructose to D-psicose and D-allose to a final D-psicose content of 0.5 to 17.0% of the sugar content and a final D-allose content of 0.2 to 10.0% of the sugar content as the active components.

(c) An amelioration agent of insulin resistance, containing a sugar mixture produced from an isomerized sugar syrup as a sugar mixture containing D-glucose and D-fructose as the main components or a starting material D-glucose and/or D-fructose, by transforming D-glucose and/or D-fructose to D-psicose and D-allose to a final D-psicose content of 0.5 to 17.0% of the sugar content and a final D-allose content of 0.2 to 10.0% of the sugar content as the active components.

(d) A low-calories sweetener containing a sugar mixture produced from an isomerized sugar syrup as a sugar mixture containing D-glucose and D-fructose as the main components or a starting material D-glucose and/or D-fructose, by transforming D-glucose and/or D-fructose to D-psicose and D-allose to a final D-psicose content of 0.5 to 17.0% of the sugar content and a final D-allose content of 0.2 to 10.0% of the sugar content as the active components.

(e) A sugar-like sweetener containing a sugar mixture produced from an isomerized sugar syrup as a sugar mixture containing D-glucose and D-fructose as the main components or a starting material D-glucose and/or D-fructose, by transforming D-glucose and/or D-fructose to D-psicose and D-allose to a final D-psicose content of 0.5 to 17.0% of the sugar content and a final D-allose content of 0.2 to 10.0% of the sugar content as the active components.

Advantages of the Invention

In accordance with the invention, a sugar mixture comprising a definite amount of an target hexose and having a sugar constitution different from that of a starting sugar material can be produced from a starting liquid sugar material. With attention focused on the physiological actions of a specific hexose, a sugar composition containing the specific hexose can be produced. By transforming hexose to a sugar of a structure different from that of a starting sugar material in a system in the presence of a basic ion exchange resin, an alkali or a calcium salt, a sugar mixture of a different sugar constitution can be produced.

More specifically, an isomerized sugar syrup of a transformation type comprising D-psicose and D-allose can be produced from an "isomerized sugar syrup" broadly defined by a sugar mixture containing D-glucose and D-fructose as the main components.

In accordance with the invention, a novel process of producing a sugar composition containing the rare sugar hexose can be established, with attention focused on the physiological actions of the rare sugar hexose, so that the problems of conventional enzymatic production processes of rare sugar hexose can be overcome. Furthermore, problematic coloring and difficulty in purification regarding conventional hexose isomerization reactions under alkaline conditions can be overcome, so that the production of rare sugar hexose by a chemical process is achieved. Because reaction, neutralization and ion removal (desalting) can be executed at a single step using ion exchange resins, the needed steps can greatly be reduced. By passing an alkali continuously through the reaction resin, further, the reactivity of the ion exchange resin can be enhanced. In such manner, a sugar mixture comprising a high ratio of a rare sugar exerting functions can be obtained, where the coloring is suppressed. Because the reduction of the resin reactivity is suppressed by passing an alkali solution through the resin, a continuous reaction can be achieved. Additionally, the amount of a resin to be used for purification can be suppressed to $1/10$ fold or less the amount of the resin to be used for purifying a browned material via batch-wise processes. By using the inventive process, the steps of preparing the required enzymes can be omitted, while problems in enzymatic productions, namely contamination of enzymes or enzyme-generating bacteria and leakage thereof are never concerned. Still additionally, rare sugar hexose inexpensive for safe use in pharmaceutical products or pseudo-pharmaceutical products, oral compositions, cosmetics and foods can be provided in accordance with the invention.

In accordance with the invention, a sugar composition comprising a specific hexose can be provided with attention focused on the physiological actions of the specific hexose, together with a pharmaceutical product or pseudo-pharmaceutical product, an oral composition, a cosmetics and a food using the sugar composition.

More specifically, a sugar composition containing D-psicose and D-allose can be provided with attention focused on the physiological actions of D-psicose and D-allose, together with an anti-obesity agent, an appetite suppressant, an amelioration agent of insulin resistance, a low-calories sweetener, or a sugar-like sweetener using the sugar composition.

The characteristic profile and use of compositions obtained via hexose isomerization was examined. Consequently, it was found that a sugar composition comprising D-psicose and D-allose had excellent physiological activities. In other words, it was found that a composition comprising D-psicose preferably at 0.5 to 17.0% of the sugar content and D-allose at 0.2 to 10.0% thereof exerted excellent characteristic properties applicable to pharmaceutical products and the like. As to the process of producing these compositions, a process using the Lobry de Bruyn and Alberda van Ekenstein transformation is great. It was revealed that such process using ion exchange resins was particularly the most suitable. By such process, assimilable sugars, for example isomerized sugar and sugar can get characteristic profiles as excellent sweeteners, anti-obesity agents, appetite suppressants, amelioration agents of insulin resistance, and low-calories sweeteners. Particularly, the composition obtained has a more excellent anti-obesity effect than those of monosaccharides having been known so far. Despite the low calories, the composition has a novel characteristic profile such as anorexigenic action. Furthermore, the sweetness thereof is so close to that of sugar and the calories thereof are so low that the composition can widely be used as a low-calories sweetener.

BEST MODE FOR CARRYING OUT THE INVENTION

Figure 1:
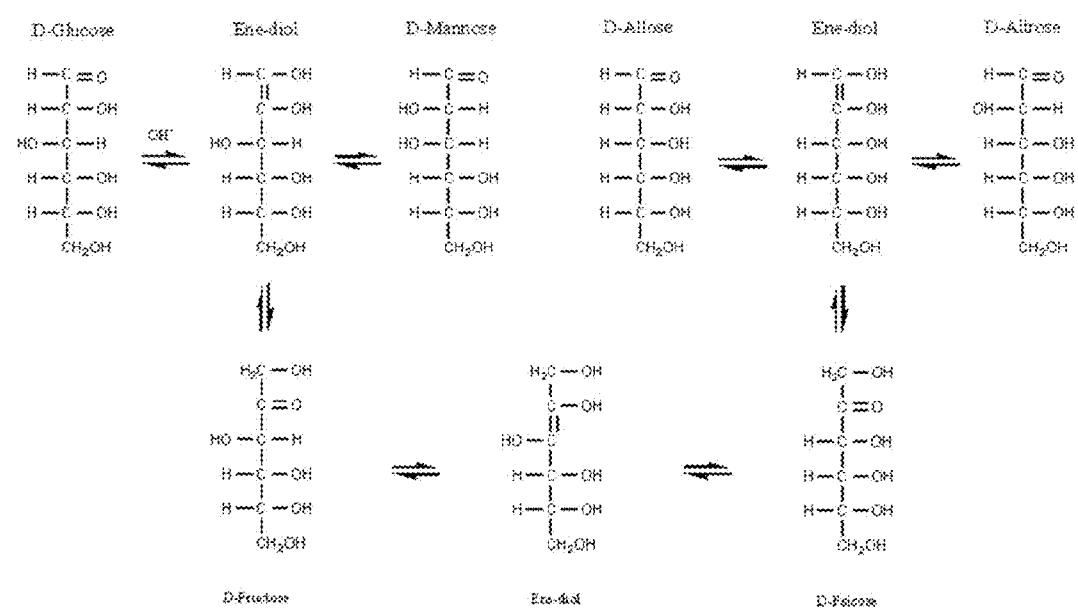
FIG. 1 A chart depicting the Lobry de Bruyn and Alberda van Ekenstein transformation.
Figure 2:
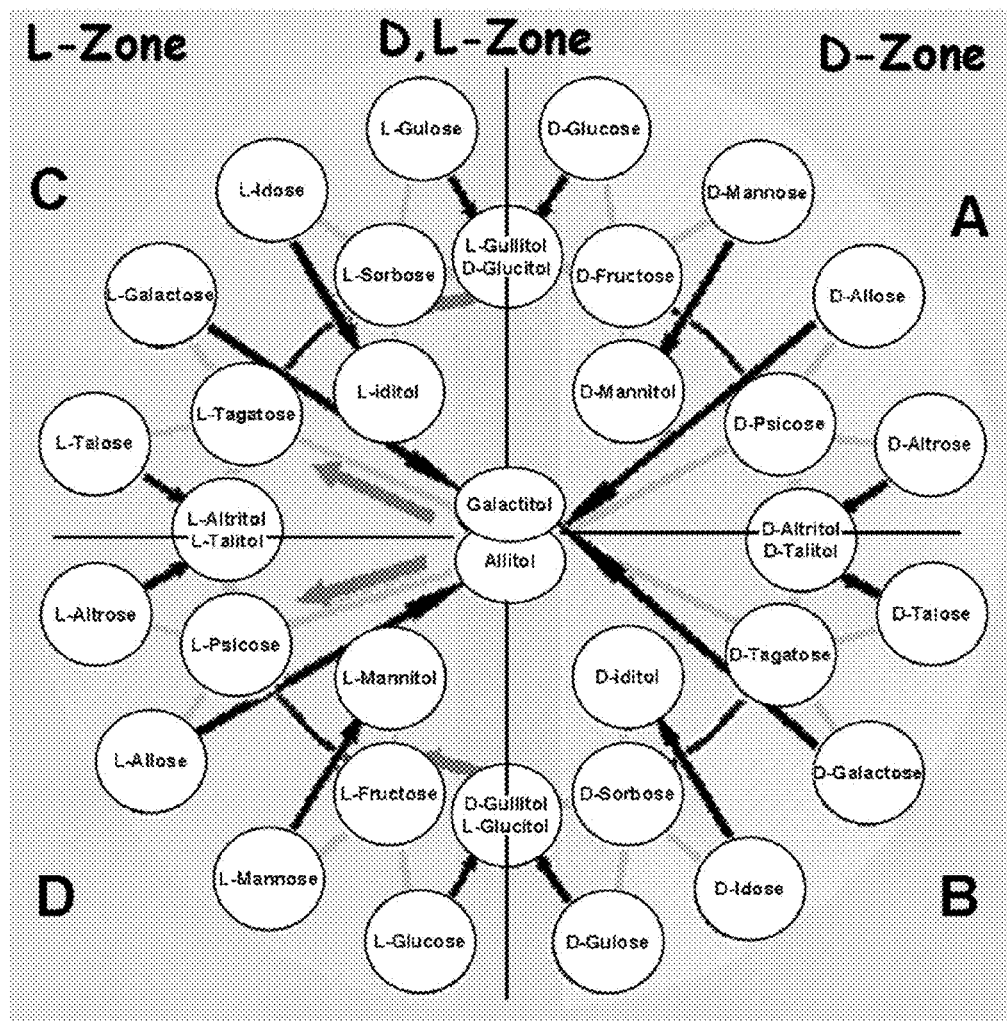
FIG. 2 A chart depicting the Izumoring of hexose.

The invention is characteristic in that a sugar mixture comprising a definite amount of an target hexose and having a sugar constitution different from that of a starting sugar material, for example a sugar mixture comprising D-psicose and D-allose and having a sugar constitution different from that of a starting sugar material, can be obtained from a starting liquid sugar material comprising hexose or a mixture comprising hexose, for example D-glucose or D-fructose and a sugar mixture thereof (for example isomerized sugar syrup) as a starting sugar material.

In accordance with the invention, the units w/v and w/w were used for the concentration of sugar solutions. For preparation of sugar solutions for reactions in the Examples, the unit w/v was used owing to ready preparation because isomerized sugar syrup was liquid. Regarding other concentrations, the unit w/w was used since feed compositions for animal experiments were prepared from powders and since refractometers for chromatograph and BRIX are indicated in w/w.

The sugar mixture comprising D-psicose and D-allose and having a sugar constitution different from that of a starting sugar material is a composition at a composition ratio between D-psicose at 0.5 to 17.0%, preferably 1 to 15% and D-allose at 0.2 to 10.0%, preferably 0.4 to 8% of the sugar content. At the constitution, the sugar mixture is applicable as a great sweetener. Additionally, for example, such composition comprising D-psicose at 2.3% or more and D-allose at 1.3% or more exerts characteristic profiles usable as anti-obesity agents, appetite suppressants, and amelioration agents of insulin resistance. For using the sugar mixture as a low-calories sweetener, the sugar mixture is at lower calories as the content of D-psicose is higher. In view of the reaction efficiency (reaction time), D-psicose and allose to be generated for a reaction time of about one hour are at about 7% and 5%, respectively. In view of them, a sugar mixture of a composition comprising D-psicose at 2.5 to 8% and D-allose at 1.5 to 5% of the sugar content is more preferable.

In accordance with the invention, an target rare sugar hexose can be produced by passing a hexose solution as a starting liquid sugar material together with an alkaline solution through a basic ion exchange resin packed in a column, and a composition comprising an target rare sugar hexose, for example D-psicose and D-allose, can be produced in the presence of an alkali or a calcium salt.

[Hexose as a Starting Sugar Material]

The hexose as a starting sugar material may be D-form or L-form in accordance with the invention. Otherwise, the hexose may be an aldose such as D-glucose or a ketose such as D-fructose. Additionally, a mixture of an aldose and a ketose may be satisfactory. From the aspect of the raw material cost, particularly, a glucose/fructose liquid sugar (isomerized sugar syrup) is advantageous. By linking the process with production plants for glucose generation with amylase from starch and isomerized sugar generation with glucose (xylose) isomerase, additionally, the steps can be omitted while advantages of scale merits can actively be taken. There are many types of glucose isomerase which react in relatively alkaline regions, so such types may be used after immobilization on anion exchange resins. In this view, the inventive composition is preferably produced under alkaline conditions while glucose is isomerized with an enzyme, in light of industrial efficiency.

Since an equilibrium reaction due to the Lobry de Bruyn and Alberda van Ekenstein transformation is applied to the reaction, any of D-fructose, D-glucose, D-psicose, D-mannose, D-allose and D-altrose or sugar mixtures thereof are obtained from these sugars. Any of D-tagatose, D-talose, D-galactose, D-sorbose, D-gulose and D-idose or sugar mixtures thereof are obtained from these sugars. Regarding the L forms, the same reaction proceeds. This indicates that in case that the Izumoring in the report paper as the non-patent reference 4 is divided into four blocks, namely upper right block (A), lower right block (B), upper left block (C) and lower left block (D), other sugars in such single block can be generated by using any sugar in the block by the process.

From the standpoint of the physiological actions of a sugar composition and with attention focused on the physiological actions of a specific hexose, a sugar composition containing the specific hexose can be produced.

In other words, a mixture comprising one or more hexose types selected from the group consisting of D-fructose, D-glucose, D-psicose, D-mannose, D-allose and D-altrose as starting sugar materials is used to produce one or more hexose types selected from the group consisting of any of D-fructose, D-glucose, D-psicose, D-mannose, D-allose and D-altrose, or sugar mixture comprising them, where the produced one or more hexose types are different from the starting sugar material.

As the mixture with a hexose as a starting sugar material, for example, a liquid sugar containing D-glucose and D-fructose can be used. With no specific limitation to the content ratio of the two sugars, the mixture can be used. Generally, a sugar mixture of D-glucose and D-fructose at a specific constitution ratio is called isomerized sugar syrup. The isomerized sugar syrup in accordance with the invention is broadly defined by a sugar mixture containing D-glucose and D-fructose as the main components. From the standpoint of availability, commercially available glucose/fructose liquid sugar, fructose/glucose liquid sugar or mixtures of D-glucose and D-fructose or sucrose hydrolyzed may preferably be used as the starting material (the raw material) in accordance with the invention.

In accordance with the invention, the isomerized sugar syrup is a liquid sugar containing glucose and fructose as the main components as produced by isomerizing a sugar solution mainly comprising glucose as obtained by hydrolysis of starch with enzymes such as amylase or with acids, including "glucose/fructose sugar syrup" at a fructose content (the ratio of fructose among sugars) less than 50%, "fructose/glucose sugar syrup" at a fructose content at 50% ore more to less than 90%, "high ratio fructose sugar syrup" at a fructose content of 90% or more, and "sucrose-mixed fructose/glucose sugar syrup" produced by adding sucrose at an amount never exceeding the amount of a glucose/fructose sugar syrup to the glucose/fructose sugar syrup. These classifications are according to the JAS Standards.

Using a mixture comprising one or more hexose types selected from the group consisting of D-tagatose, D-talose, D-galactose, D-sorbose, D-gulose, and D-idose as a starting material hexose, a mixture comprising one or more hexose types selected from the group consisting of D-tagatose, D-talose, D-galactose, D-sorbose, D-gulose, and D-idose or sugar mixture comprising them can be produced, where the produced one or more hexose types are different from the starting sugar material.

Using a mixture comprising one or more hexose types selected from the group consisting of L-fructose, L-glucose, L-psicose, L-mannose, L-allose and L-altrose as a starting material hexose, a mixture comprising one or more hexose types selected from the group consisting of L-fructose, L-glucose, L-psicose, L-mannose, L-allose and L-altrose or sugar mixture containing them can be produced, where the produced one or more hexose types are different from the starting sugar material.

Using a mixture comprising one or more hexose types selected from the group consisting of L-tagatose, L-talose, L-galactose, L-sorbose, L-gulose, and L-idose as a starting hexose material, a mixture comprising one or more hexose types selected from the group consisting of L-tagatose, L-talose, L-galactose, L-sorbose, L-gulose, and L-idose or sugar mixtures containing them can be produced, where the produced one or more hexose types are different from the starting sugar material.

As described in the non-patent reference 3, however, a possibility remains that a sugar over a block may sometimes be produced through sugar cleavage and reverse aldol condensation. A pathway A→B, namely D-glucose→D-sorbose is one example. In accordance with the invention, mild reaction conditions for preferentially progressing an intra-block reaction to hardly progress an inter-block reaction was found and is used.

Still further, some of disaccharides, trisaccharides and oligomers may be isomerized. Using the reaction, in particular, a hexose at an end group in disaccharides, trisaccharides, oligosaccharides, dextrin and the like may be isomerized. For example, lactose (galactose-glucose) may be isomerized to produce disaccharides such as lactulose (galactose-fructose) and galactose-psicose.

Further, sugar mixture may be obtained by reaction of a great number of hexose types. By hydrolyzing lactose and isomerizing the hydrolyzed product by the process, D-fructose, D-glucose, D-psicose, D-mannose, D-allose, D-altrose, D-tagatose, D-talose, D-galactose, D-sorbose, D-gulose and D-idose can be obtained. [Concentration of a Starting Liquid Sugar Material]

As to the concentration of a starting liquid sugar material, a preferable range resides in a concentration as high as possible when the subsequent concentration procedure is taken into account. Because the yield of a rare sugar hexose can be raised as the concentration of a starting liquid sugar material is lower, the concentration of a starting liquid sugar material is 5% to 90%, preferably 10% to 60%, most preferably 20% to 40% in view of the production efficiency. It is considered that in case that the concentration is high (in case of a lower water content), less byproducts are produced. Via the adjustment of the concentration, the ratio of products may be modified to obtain a sugar mixture. For example, a starting liquid sugar material at a concentration of 100%, namely so-called powder may be sprayed with an alkali, to produce a rare sugar hexose.

[Ion Exchange Resin]

As to the concentration of a sugar solution (a liquid sugar material), a concentration thereof at 5 w/w % or more is preferable in light of subsequent concentration procedure. Depending on the separation conditions for chromatography, the concentration may be modified. So as to prevent suspension of such resins, the concentration is more preferably about 5 to 30%. For reaction with a sugar solution at 60%, a needed amount of an alkali is increased about 2.5 fold. In view of advantages such as less concentration, reaction at a concentration of 30 to 60% is a preferable condition.

As the basic ion exchange resin for use in accordance with the invention, primary amines, secondary amines, tertiary amines, quaternary amines and the like are used as the functional groups. Among them, quaternary amines are preferable.

As the support, various supports are available. However, porous type is more preferable than gel form. Additionally, more ion exchange groups per support are more preferable. More specifically, experimental results show that the reaction efficiency is higher when a resin is used than when no resin is used; and that OH-form resins are at higher efficiency than Cl-form resins (see FIG. 8). It is also indicated that the reaction efficiency is higher with a mother resin of porous form than with a mother resin of gel form and that the reaction efficiency is higher when the total ion exchange volume is larger than when the total ion exchange volume is smaller (see FIGS. 8 and 9).

[Alkalis and Calcium Salts]

As the alkaline solutions for use in accordance with the invention, sodium hydroxide, potassium hydroxide, ammonia, calcium hydroxide, calcium oxide, barium hydroxide, lead hydroxide, strontium hydroxide, magnesium hydroxide, tin hydroxide, and aluminium hydroxide may appropriately be used. In view of safety profile and cost, sodium hydroxide and calcium hydroxide are preferable.

The optimal concentration of an alkali depends on the presence of an ion exchange resin. Generally, the alkali is preferably contained at 0.005 mol/l or more in a hexose solution.

When a strongly basic ion exchange resin is used, in accordance with the invention, no alkali is essentially needed. Hexose transformation may progress with a strongly basic ion exchange resin alone.

Furthermore, the patent reference 3 describes the isomerization of D-glucose using calcium chloride. Using the catalytic action of calcium ion, in accordance with the invention, isomerization is initiated. The isomerization of hexose progresses in the presence of a calcium salt generating calcium ion, for example calcium chloride; from D-fructose, for example, a sugar composition containing D-psicose and D-allose can be produced. Preferably, calcium salts exist in the co-presence of an alkali and are preferably contained at 0.005 mol/l or more in a sugar solution. In a system in the presence of a calcium salt, the co-presence of a basic ion exchange resin is not necessarily needed.

[Production Step of Hexose using a Basic Ion Exchange Resin]

In accordance with the invention, the structure of a hexose type can be transformed to that of another hexose type with a basic ion exchange resin, in spite of the presence or absence of an alkali. When an alkali is used, advantageously, a reaction column can be used continuously. The invention is characteristic in that hexose can be isomerized with basic ion exchange resins.

In general sugar manufacture industries, the desalting step post-reaction generally comprises passing the resulting solution through an acidic ion exchange resin so as to prevent extra secondary reactions under alkaline conditions, passing the flow-through fraction through a basic ion exchange resin and finally passing the flow-through fraction through a mix resin. By arranging the general flow-through steps in a reverse manner, byproducts generated by secondary reactions are obtained as the main product (the target hexose).

The transformation of glucose and fructose to rare sugars under alkaline conditions is carried out on a basic ion exchange resin; then, an acidic ion exchange resin is used for neutralization and ion exchange; and the resulting flow-through fraction is passed through a mix resin. The resin to be used in that case is generally any resin with acidic or alkaline properties and with ion exchange capacities, with no specific limitation. The final mix resin is not necessarily needed, depending on the production purity. By appropriately adding a purification step, the purity of the product may be adjusted. When needed, purification with a basic ion exchange resin may satisfactorily be added.

It is particularly notable that the reaction efficiency may be reduced due to the adsorption of the starting sugar material and acidic byproducts on the resin in the reaction course, but the inventors found that the problem could be overcome by keeping the starting sugar material at alkalinity from the start to suppress the reduction of the efficiency.

Regarding the upper limit of the concentration of an alkaline solution, a concentration never involving the generation of byproducts is preferable. Depending on the conditions for using a resin, the concentration is defined. Regarding the lower limit, a concentration of 0.005 mol/l or more is preferable as the concentration sufficiently producing a reaction product. The most preferable alkali concentration in case that an ion exchange resin is used is 0.005 mol/l to 2 mol/l. In the Examples, alkaline solutions within a range of 0.0029 mol/l to 0.1 mol/l were used.

Regarding the reaction temperature, it is preferably 20° C. or more, more preferably 40° C. to 70° C. for passing solutions through resins. By modifying the reaction temperature, the alkali concentration and the concentration of the raw material, the constitution of the produced composition can be adjusted. Via the preparation of the constitution, the composition adjusted of the calories for human intake can be obtained. It is reported (non-patent reference 5) that the energy value of D-psicose in particular is zero kilocalorie. Adjustment of D-psicose content can reduce the calories, depending on the amount of D-psicose.

Like methods described in the report paper as the non-patent reference 6 and the like, a method comprising pressurization to promote isomerization is disclosed. The productivity may be improved via pressurization in accordance with the process. Depending on the production scale, further, the inventive composition may also be obtained by using resins under batch-wise conditions or singly using alkalis with no use of resins.

According to the patent reference 4, further, the composition at a D-psicose content at 8 or more of the sugar content can be used as an anti-obesity agent. The report of the non-patent reference 7 describes that the composition of a D-psicose content at about 9 of the sugar content is used as a post-meal blood sugar-reducing agent. The sugar mixture obtained by the isomerization and ion exchange in accordance with the invention may possibly contain a rare sugar, particularly D-psicose at 8 or more, so the sugar mixture can be provided with no fractionation, as a material with functions such as an anti-obesity action, a post-meal blood sugar-reducing action and the like.

After passing through an ion exchange resin, the reaction solution may be subjected to sugar separation by column chromatography, or may be precipitated and separated using a chemical chelating agent with sugars. By the inventive reaction process, no significant browning occurs before column separation. In view of column life, generally known purification steps such as deodorization and discoloring courses with active charcoal may be added. Regarding chromatography, simulated moving bed chromatography (see patent references 5 and 6) is the most optimal for the purpose, but the separation mode is not specifically limited. From the composition produced in accordance with the invention, D-psicose and D-allose may satisfactorily be fractionated on chromatograms to obtain D-psicose and/or D-allose.

Figure 3:
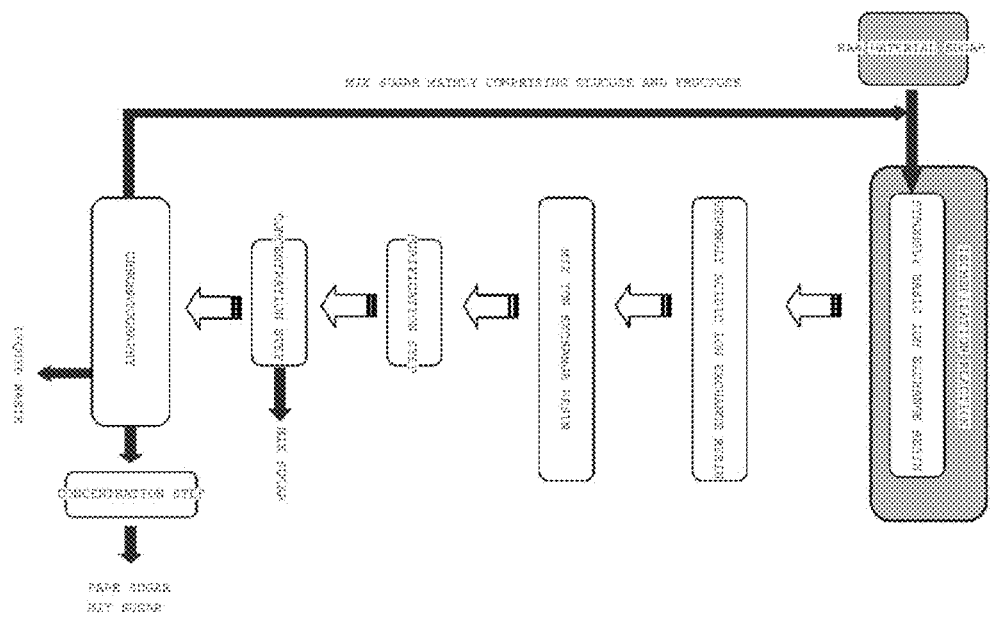
FIG. 3 A schematic view depicting and explaining the inventive process.

Non-aimed sugars remaining after the separation of the target sugar may be reused. For example, such sugars may be added to the starting sugar material, which is then introduced into a basic ion exchange resin as a reaction medium. By such continuous plant, the needed steps can be omitted. Preferable embodiments of the invention are depicted in FIG. 3.

The rare sugar obtained herein can be provided as a material with functions such as anti-obesity action and post-meal blood glucose-reducing action.

[Production Step of Hexose using Alkalis or Calcium Salts]

In accordance with the invention, a hexose type can be transformed to a hexose type of another structure, with no use of any ion exchange resins. For example, a composition containing D-psicose and D-allose can be produced from hexose. By mixing a hexose type with an alkali or a calcium salt to prepare a co-present state and then treating the mixture under heating within a range of 25° C. to 100° C., the raw material hexose can be transformed to a sugar composition comprising D-psicose and D-allose as other hexose types. The temperature for the heating treatment is particularly preferably 40° C. or more. A calcium salt is preferably contained at a concentration of 0.005 mol/l to 6 mol/l in a sugar solution, while an alkali such as sodium hydroxide is preferably contained at a concentration of 0.005 mol/l to 2 mol/l therein. By the process using an alkali or a calcium salt, a sugar comprising D-allose at 0.5 to 5.0% of the total sugar content and D-psicose at 3.0% to 7.0% thereof in the resulting sugar composition is produced. The production step comprises a simple step comprising a mixing and heating treatment, to which either mode of batch-wise mode or continuous mode may be applicable.

[Novel Sugar Composition containing D-Psicose and D-Allose]

With attention focused on the physiological actions of a specific hexose, a sugar mixture produced for the purpose of obtaining a sugar composition comprising the specific hexose by the inventive process is a novel sugar composition.

In case that an isomerized sugar of a transformation type comprising D-psicose and D-allose as target hexoses is produced from an "isomerized sugar" broadly meant by a sugar mixture comprising D-glucose and D-fructose as the main components, a sugar mixture comprising definite amounts of the target hexoses produced and having a sugar constitution different from that of the starting sugar material is a novel sugar composition.

By determining the content of an target hexose in the sugar content depending on the type and level of an target function, the mode for using the same and the amount of the same to be used, and treating a starting sugar material under the most optimal production conditions for the purpose of obtaining the target hexose, a sugar mixture of an target composition can be produced. By treating an isomerized sugar syrup as a sugar mixture comprising D-glucose and D-fructose as the main components as the starting sugar materials or a starting liquid sugar material comprising D-glucose and/or D-fructose in a system in the presence of one or more types selected from the group consisting of basic ion exchange resins, alkalis and calcium salts, an isomerization reaction progresses as an equilibrium reaction for transforming D-glucose and D-fructose as the starting sugar materials to target D-psicose and D-allose, so that a sugar composition comprising D-psicose and D-allose and having a sugar constitution different from the raw material isomerized sugar can be produced, of which the constitution comprises D-psicose at 0.5 to 17.0% of the sugar content and D-allose at 0.2 to 10.0% thereof. Characteristically, the hexose composition concurrently contains D-psicose and D-allose, which is for example of a hexose constitution preferably comprising D-psicose at 1.0 to 15.0% of the sugar content and D-allose at 0.4 to 8.0% thereof and most preferably comprising D-psicose at about 2.5 to 8.0 of the sugar content and D-allose at 1.5 to 5.0% thereof. The hexose composition in which D-psicose and D-allose concurrently exist exerts a remarkable effect and exerts an unexpected synergistic effect on comparison with the effect of D-psicose or D-allose alone. As physiological effects, for example, excellent such effects are exerted. Such synergistic effects are verified in Examples 31 to 33. Regarding body weight decrement ratio, body fat decrement ratio and feed intake decrement ratio, in particular, the specific effects of the invention are exerted. In case that the sugar composition containing D-psicose and D-allose in accordance with the invention is ingested, the reduction of blood sugar level and the reduction of insulin level can be observed. The reduction of insulin level with the sugar composition of the invention is an effect never having been known so far at tests of single intake of D-psicose or D-allose.

As to the ratios of D-psicose and D-allose in the total sugar material in order that the hexose composition of the invention can exert the excellent effects described above, the ratio of D-psicose in the total sugar is 0.5 to 15.0% and preferably 1.0 to 15.0%, while the most preferable range of D-psicose is 2.5 to 8%; the ratio of D-allose in the total sugar is 0.2 to 10.0% and preferably 0.4 to 8.0%, while the most preferable range thereof is 1.5 to 5.0%.

The total amount of D-psicose and D-allose is within a range of 0.7 to 25.0%, preferably 1.0 to 20.0%. The total amount of D-psicose and D-allose is within a range of 0.7 to 25.0%, preferably 1.4 to 23.0%, most preferably 4.0 to 13.0%.

[Use of Hexose Composition]

Using the process of the invention, inexpensive rare sugar hexose can be provided for safe use in pharmaceutical products or pseudo-pharmaceutical products, oral compositions, cosmetics and foods.

In accordance with the invention, additionally, sugar compositions containing a specific hexose with attention focused on the physiological actions of the specific hexose can be provided, together with pharmaceutical products or pseudo-pharmaceutical products, oral compositions, cosmetics and foods using the sugar compositions.

More specifically, sugar compositions containing D-psicose and D-allose can be provided with attention focused on the physiological actions of D-psicose and D-allose, together with anti-obesity agents, appetite suppressants, amelioration agents of insulin resistance, low-calories sweeteners, or sugar-like sweeteners using the sugar compositions. The hexose composition according to the process of the invention can be used in any one of those requiring sweetness or functionality, such as foods, health foods, foods for patients, food materials, health food materials, food materials for patients, food additives, health food additives, food additives for patients, drinks, health drinks, drinks for patients, drinking water, health drinking water, drinking water for patients, pharmaceutical agents, raw materials for pharmaceutical preparation, feeds, and feeds for sick cattle and/or feeds for sick animals.

The characteristic profiles and use of the compositions obtained by hexose isomerization were examined. Consequently, it was found that the compositions comprising D-psicose and D-allose had great physiological activities. In other words, it was found that the composition comprising D-psicose and D-allose, specifically D-psicose at 0.5 to 15.0% of the sugar content and D-allose at 0.2 to 10.0% thereof exerted excellent characteristic properties applicable to pharmaceutical products and the like. As the process of producing such composition, a process using the Lobry de Bruyn and Alberda van Ekenstein transformation is great. It was clearly shown that such process additionally using ion exchange resins was particularly the most optimal. By such process, excellent characteristic properties as sweeteners, anti-obesity agents, appetite suppressants, amelioration agents of insulin resistance, and low-calories sweeteners can be definite to assimilable sugars, for example isomerized sugars and sugar. Particularly, the obtained compositions have excellent anti-obesity effects than those of monosaccharides having been known so far. Despite the low calories, further, the compositions have novel characteristic properties such as anorexigenic actions. Furthermore, the sweetness of the compositions is close to that of sugar and has low calories, so that the compositions are widely applicable as low-calories sweeteners.

In case of utilizing the hexose of the invention in foods, the hexose may be used as it is or may be prepared into forms such as oil dilution forms and emulsion forms or forms with addition of carriers for general use in food industries. The drink forms are non-alcohol drinks or alcohol drinks. The non-alcohol drinks include for example carbonate drinks, fruit juice drinks, non-carbonate drinks such as nectar drinks, refreshing drinks, sport drinks, tea, coffee and cocoa. The alcohol drink forms include for example pharmaceutical Japanese sake, shochu (distilled liquor from sweet potatoes, rice, buckwheat, etc.) diluted with carbonate drinks, ume (Japanese apricot) dipped in shochu (ume-shu), beer, foaming beer, and third-generation beer in common food forms.

The forms of the composition (hexose) of the invention to be used as food materials or food additives or pharmaceutical agents for the purpose of ameliorating abnormal sugar metabolism and/or abnormal lipid metabolism include for example solids such as tablets, capsules, powders or granules to be dissolved in drinks, semi-solids such as jellies, liquids such as drinking water, and high-concentration solutions for use after dilution.

By appropriately adding the hexose composition of the invention to foods, further, health foods or patients' foods can be prepared for the purpose of ameliorating abnormal sugar metabolism and/or abnormal lipid metabolism. As optional components, additionally, vitamins, carbohydrates, dyes and flavor to be generally added to foods may appropriately be blended. Foods can be ingested in appropriate forms such as liquids or solids. The hexose composition can be ingested as soft capsules produced by encapsulating the hexose composition with gelatin and the like. The capsules can be prepared from gelatin films prepared by adding water to a raw material gelatin and adding plasticizers (glycerin, D-sorbitol, etc.) to the resulting mixture.

The hexose of the invention can be used in tea, coffee, seasonings [mirin (sweet sake for seasoning), etc.] and the like.

The drinks and foods specifically include those described below: confectionaries (purine, jelly, goumi candies, candies, drops, caramel, chewing gum, chocolate, pastry, butter cream, custard cream, chou ala cream, hot cake, bread, potato chips, fried potato, pop corn, biscuit, cracker, pie, sponge cake, pao de Castella, waffle, cake, doughnut, biscuit, cookies, rice cake seasoned with soy sauce, sliced and dried rice cake, sweet rice cake, buns with bean jam fillings, candies), dried noodle products (macaroni, pasta), egg products (mayonnaise, fresh cream), drinks (functional drinks, lactic acid beverage, lactic acid bacteria beverage, concentrated milk drinks, fruit juice drinks, non-fruit juice drinks, flesh fruit drinks, clear carbonate drinks, fruit juice-added carbonate drinks, fruit-colored carbonate drinks), favorites (green tea, tea, instant coffee, cocoa, canned coffee drinks), dairy products (ice cream, yoghurt, coffee milk, butter, butter sauce, cheese, fermented milk, processed milk), pastes (marmalade, jam, flower paste, peanut paste, fruit paste, syrup-dipped fruit), cattle products (ham, sausage, bacon, dry sausage, beef jerky, lard), fishes and shellfishes (fish ham, fish sausage, fish paste cake, tube-shaped fish paste cake, cake of pounded fish, dry fish, dried bonito, dried mackerel, small dried sardines, sea urchin, salted squad guts, dried squad, dried and sweet sake-seasoned fish, dried shellfish, smoked salmon and the like), foods boiled down in soy sauce (small fish, shellfishes, wild vegetables, mushroom, kombu (kelp)), curries (instant curry, retort curry, canned curry), seasonings (soybean paste, powdered soybean paste, soy sauce, powdered soy sauce, unrefined sake (moromi), fish soy sauce, Worcestershire sauce, ketchup, oyster sauce, solid bouillon, dip for grilled meat, curry roux, stew stocks, soup stocks, Japanese soup stocks, paste, instant soup, seasoned powder for sprinkling over rice, dressings, salad oil), fried products (fried soybean curd, fried confectionaries, instant Chinese noodle), soybean milk, margarine, shortening and the like.

The drinks and foods described above can be produced by blending the hexose composition with raw materials for general foods by general processes. Generally, the amount of the composition to be blended in the foods and drinks is preferably 0.1 to 20% by weight, with no specific limitation, but the amount thereof depends on the food form. Additionally, the foods and drinks may be used as functional foods, nutrition supplemental foods or health foods. The forms thereof are not limited. As production examples of foods, for example, mixtures with proteins with good amino acid balance, such as highly nutritious milk protein, soybean protein and egg albumin and decomposition products thereof, egg white oligopeptide and hydrolyzed soybean products, and additional mixtures with single one of amino acids can be used according to general processes. Furthermore, the hexose composition may be used in forms of soft capsules and tablets.

Examples of the nutrition supplemental foods or functional foods include processed forms such as fluid foods, semi-ingested nutritious foods, component nutritious foods, drinks, capsules and enteral nutritious foods blended with sugars, fat, microelements, vitamins, emulsifiers and flavor. So as to improve nutrition balance and flavor, various foods described above, for example sport drinks and nutritious drinks are blended with nutritious additives such as amino acids, vitamins and minerals, sweeteners, spice, flavor and dyes.

The inventive composition is applicable as feeds for cattle, chicken and pets. The composition can be blended in for example dry dog food, dry cat food, wet dog food, wet cat food, semi-moist dog food, feeds for poultry, cattle feeds for cow and pig. The feeds by themselves can be prepared by general processes.

These therapeutic agents and prophylactic agents can also be used for animals except humans, for example cattle mammals such as cow, horse, pig and sheep, domestic fowls such as chicken, quail and ostrich, pets such as reptile, birds or small mammals, and cultivated fishes.

The sugar mixture of the invention is mixed with sweeteners at high sweetness level such as aspartame, and sweeteners such as sugar alcohol, ketose, and aldose for adjusting the sweetness.

Pharmaceutical agents comprising the hexose composition of the invention for the purposes of the effect on the amelioration of abnormal sugar metabolism and/or abnormal lipid metabolism and of the effect on the obesity amelioration may be used singly or may be blended with appropriate additives such as common excipients, stabilizers, preservatives, binders and disintegrators, to be formulated into appropriate pharmaceutical forms such as liquids, granules, fine granules, powders, tablets, capsules, pills, ointments, patches, sprinkling agents, spray agents or injections, for oral, trans-nasal, trans-dermal and intravenous administration.

So as to prepare the inventive composition as a pharmaceutical agent, additionally, organic or inorganic solids, semi-solids or liquid carriers for pharmaceutical use, dissolution agents or diluents suitable for oral, trans-nasal, trans-dermal and intravenous administration can be used. All of water, gelatin, lactose, starch, magnesium stearate, talc, animal and vegetable oils, benzyl alcohol, gum, polyalkylene glycol, petroleum resins, coconut oil, lanolin or other carriers for use in pharmaceutical products can be used as carriers for pharmaceutical agents containing the inventive composition. Furthermore, stabilizers, moistening agents, emulsifiers, and salts for modifying osmotic pressure and for maintaining pH appropriate for the blends may appropriately be used as supplementary pharmaceutical agents.

For pharmaceutical preparation of cosmetics and the like, still additionally, soluble films have been used. For the purpose of refreshing and preventing oral odor, edible and soluble films are used as flavor film with flavor retained thereon and the like. Designs such as cosmetic films with moisturizers for use as packs, or cosmetic films to be dissolved in water for use as emulsion are proposed. Furthermore, examination is now made about soluble films with anti-inflammation agents for use as fomentations. A soluble film with excellent dissolution properties and characteristic film properties as a packing agent for foods and pharmaceutical products or as a carrier for retaining foods or the active ingredients of pharmaceutical products is proposed, and the soluble film is preferably used for such use (patent reference 7). In such manner, the hexose composition of the invention is applicable to pharmaceutical products or pseudo-pharmaceutical products, and cosmetics.

The invention is now described in more detail in the Examples. However, the invention is never limited by the Examples.

In the Examples, basic ion exchange resins of Cl type were purchased and then, the resins of Cl type were transformed to those of OH type, for use. Therefore, the basic ion exchange resins in the Examples were expressed as the basic ion exchange resins of Cl type. Except for Example 30, the basic ion exchange resins were transformed to those of OH type at experiments. For the purpose of comparing the reactions between the basic ion exchange resins of Cl type and the basic ion exchange resins of OH type, IRA900J [Cl] was used in Example 30 as it was of Cl type. Unless otherwise stated, analysis was done after reaction on basic ion exchange resins and passing the solution through strongly acidic ion exchange resins.

EXAMPLE 1

<Reaction of D-Fructose with Strongly Basic Ion Exchange Resin>

500 ml of 10 w/v % D-fructose solution was passed through 38.5 ml of a packed strongly basic ion exchange resin at a temperature of 60° C. and a flow rate of 1.6 ml/min (resin: Amberlite IRA900J[Cl], 1.5-cm inner column diameter). Then, the reaction solution eluted from the column was sampled over time for HPLC analysis (detector: RI; column: MCI GEL CK 08EC manufactured by Mitsubishi Kasei). Coloring level was measured with a spectrophotometer using a cell of an optical path width of 10 mm. The coloring level was defined as the value of [(absorbance at 420 nm)−(absorbance at 720 nm)]×10 according to BRIX10.

Figure 4:
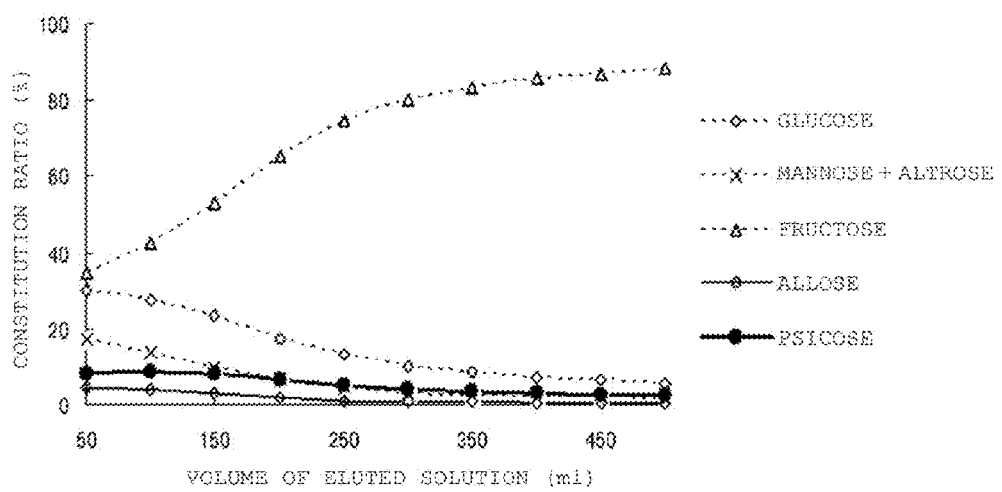
FIG. 4 Graphs depicting the analyzed composition of a sugar mixture comprising the target sugar in Example 1 entitled <Reaction of D-fructose with strongly basic ion exchange resin>.

The analyzed composition is shown in FIG. 4. The sugar composition of the solution (500 ml) after elution was D-glucose at 15.0%, (D-mannose+D-altrose) at 6.3%, D-fructose at 69.3%, D-allose at 1.8%, and D-psicose at 5.2%. Hence, a 5.2-% D-psicose solution was obtained. The coloring level was 0.05 (on a BRIX10 basis), with almost no browning change. This clearly indicates that other sugars can be obtained, starting from any of D-fructose, D-glucose, D-psicose, D-allose, D-altrose and D-mannose by the process. By the process, apparently, acidic byproducts are additionally generated, which reduces the reactivity as the solution passes through the column. The characteristic profile of the inventive composition is that the ratio of products is approximately determined on the basis of starting substances, reaction time and free energy difference (non-patent reference 4, p. 431-433) and that assimilable sugars such as D-glucose and D-fructose were produced at a ratio of several tens % and rare sugars were produced at a ratio of several Particularly, D-psicose is produced at about 15 and D-allose is produced at about 8%, by increasing the reaction time or the alkali concentration.

EXAMPLE 2

<Reaction of Isomerized Sugar with Strongly Basic Ion Exchange Resin>

500 ml of a 10 w/v % isomerized sugar solution was passed through 38.5 ml of a packed strongly basic ion exchange resin at a temperature of 60° C. and a flow rate of 1.6 ml/min (resin: Amberlite IRA900J[Cl], 1.5-cm inner column diameter). Then, the reaction solution eluted from the column was sampled over time for HPLC analysis (detector: RI; column: MCI GEL CK 08EC manufactured by Mitsubishi Kasei).

Figure 5:
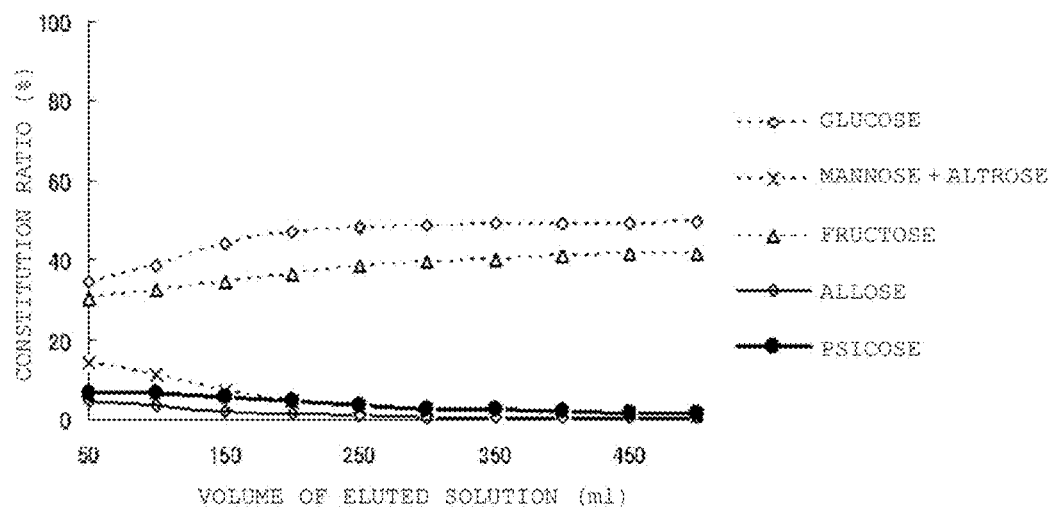
FIG. 5 Graphs depicting the analyzed composition of a sugar mixture comprising the target sugar in Example 2 entitled <Reaction of isomerized sugar syrup with strongly basic ion exchange resin>.

The analyzed composition is shown in FIG. 5. The sugar composition of the solution (500 ml) after elution was D-glucose at 45.9%, (D-mannose+D-altrose) at 4.9%, D-fructose at 37.7%, D-allose at 1.5%, and D-psicose at 3.7%. Hence, a 3.7-% D-psicose solution was obtained. The coloring level then was 0.04 (on a BRIX10 basis), with almost no browning change observed.

EXAMPLE 3

<Hexose Generation by Batch-Wise Process>

A 40-% D-fructose solution was adjusted to pH 11 for heating at 100° C. for 90 minutes by a batch-wise process. So as to maintain the pH, an appropriate volume of 4N NaOH was added every 30 minutes.

The sugar composition of the reaction solution then was D-glucose at 18.8%, (D-mannose+D-altrose) at 21.9%, D-fructose at 29.3%, D-allose at 10.0%, and D-psicose at 9.5%. Hence, a 9.5-% D-psicose solution was obtained. However, the coloring level then was 292.2 (on a BRIX10 basis). The amount of an ion exchange resin to be required for eliminating the browning change of the product was 10-fold or more the amount of the resins used in Examples 1 and 2. This indicates that the cost reduction by the process of the invention is 10-fold or more that of the batch-wise process.

EXAMPLE 4

<Reaction of D-Fructose in 0.1 mol/l NaOH Solution with Strongly Basic Ion Exchange Resin>

With 0.1M NaOH solution, D-fructose was adjusted to 10 w/v %. 500 ml of the resulting solution was passed through a strongly basic ion exchange resin and a strongly acidic ion exchange resin, in this order at a temperature of 60° C. and a flow rate of 1.6 ml/min. (The strongly basic ion exchange resin: Amberlite IRA900J[Cl]; column length: 30 cm; inner diameter: 1.5 cm). After the reaction solution eluted from the column was sampled over time, HPLC analysis (detector: RI; column: MCI GEL CK 08EC manufactured by Mitsubishi Kasei) was done.

Figure 6:
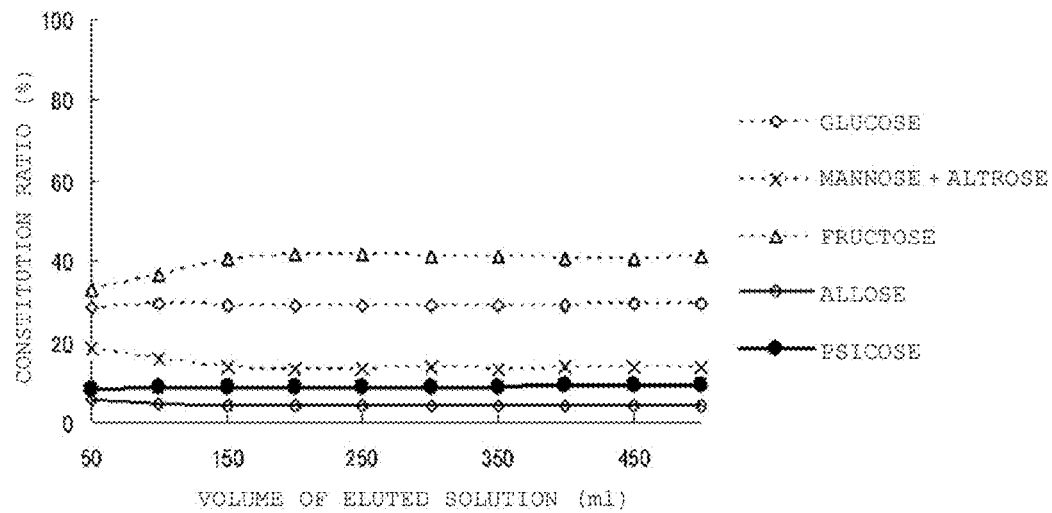
FIG. 6 Graphs depicting the analyzed composition of a sugar mixture containing the target sugar in Example 4 entitled <Reaction of D-fructose in 0.1 mol/l NaOH solution with strongly basic ion exchange resin>.

The analyzed composition is shown in FIG. 6. The sugar composition of the solution after elution was D-glucose at 29.0%, (D-mannose+D-altrose) at 14.2%, D-fructose at 39.8%, D-allose at 4.3%, and D-psicose at 8.8%. The reaction efficiency by the process using an alkali solution as a raw material was apparently never lowered. This clearly indicates that the flow of the alkali solution through the column enabled a continuous reaction on the resins and the step is integrated in the process.

EXAMPLE 5

<Reaction of D-Glucose with Strongly Basic Ion Exchange Resin>

With 0.1 mol/l NaOH solution, 500 ml of a 10-w/v % D-glucose solution was adjusted to 10 w/v %. The resulting D-glucose solution was passed through 38.5 ml of a packed strongly basic ion exchange resin at a temperature of 60° C. and a flow rate of 1.6 ml/min (the resin: Amberlite IRA900J [Cl]; inner diameter: 1.5 cm). After the reaction solution eluted from the column was sampled over time, HPLC analysis (detector: RI; column: MCI GEL CK 08EC manufactured by Mitsubishi Kasei) was done.

After elution, a sugar mixture solution (250 ml) of D-glucose, D-mannose, D-fructose, D-allose and D-psicose was obtained, with almost no browning change observed. This clearly indicates that sugars in the block A (ketose and aldose) can be obtained using D-glucose (aldose) as the starting material.

EXAMPLE 6

<Reaction of D-Fructose in 0.005 mol/l NaOH Solution with Strongly Basic Ion Exchange Resin>

With 0.005 mol/l NaOH solution, D-fructose was adjusted to 10 w/v %. 500 ml of the resulting solution was passed through a strongly basic ion exchange resin and a poorly acidic ion exchange resin, in this order at a temperature of 60° C. and a flow rate of 1.6 ml/min. (The strongly basic ion exchange resin: Amberlite IRA900J[Cl]; column length: 30 cm; inner diameter: 1.5 cm). After the reaction solution eluted from the column was sampled over time, HPLC analysis (detector: RI; column: MCI GEL CK 08EC manufactured by Mitsubishi Kasei) was done.

After elution, a sugar mixture solution of D-glucose, D-mannose, D-fructose, D-allose and D-psicose was obtained. It was revealed that the reaction efficiency of the process using 0.005 M alkali solution as a raw material was never lowered. This apparently indicates that the alkali solution passing through the column enabled a continuous reaction on the resins and the step is integrated in the process. Additionally, the concentration then was at least 0.005 M or more as a solution.

EXAMPLE 7

<Reaction of Isomerized Sugar in 0.1 mol/l NaOH solution with Strongly Basic Ion Exchange Resin>

With 0.1 mol/l NaOH solution, an isomerized sugar was adjusted to 10 w/v %. 500 ml of the resulting solution was passed through a strongly basic ion exchange resin and a poorly acidic ion exchange resin, in this order at a temperature of 60° C. and a flow rate of 1.6 ml/min. (The strongly basic ion exchange resin: Amberlite IRA900J[Cl]; column length: 30 cm; inner diameter: 1.5 cm). After the reaction solution eluted from the column was sampled over time, HPLC analysis (detector: RI; column: MCI GEL CK 08EC manufactured by Mitsubishi Kasei) was done.

After elution, a sugar mixture solution of D-glucose, D-mannose, D-fructose, D-allose and D-psicose was obtained. It was revealed that by the process using an alkali solution of the isomerized sugar as a raw material, the flow of the alkali solution through the column enabled a continuous reaction on the resins and the step is integrated in the process.

EXAMPLE 8

<Reaction of 5% Isomerized Sugar with Strongly Basic Ion Exchange Resin>

With 0.1 mol/l NaOH solution, an isomerized sugar was adjusted to 5 w/v %. The resulting solution was passed through 38.5 ml of a packed strongly basic ion exchange resin at a temperature of 60° C. and a flow rate of 1.6 ml/min. (The strongly basic ion exchange resin: Amberlite IRA900J[Cl]; inner diameter: 1.5 cm). After the reaction solution eluted from the column was sampled over time, HPLC analysis (detector: RI; column: MCI GEL CK 08EC manufactured by Mitsubishi Kasei) was done.

After elution, a sugar mixture solution (250 ml) of D-glucose, D-mannose, D-fructose, D-allose and D-psicose was obtained, with almost no browning change observed. It was revealed that sugars in the block A could be produced, using a starting sugar material in the block A even in a dilute solution of about 5%.

EXAMPLE 9

<Reaction of 30% Isomerized Sugar with Strongly Basic Ion Exchange Resin>

With 0.1 mol/l NaOH solution, the isomerized sugar was adjusted to 30 w/v %. The resulting solution was passed through 38.5 ml of a packed strongly basic ion exchange resin at a temperature of 60° C. and a flow rate of 1.6 ml/min. (The strongly basic ion exchange resin: Amberlite IRA900J[Cl]; inner diameter: 1.5 cm). After the reaction solution eluted from the column was sampled over time, HPLC analysis (detector: RI; column: MCI GEL CK 08EC manufactured by Mitsubishi Kasei) was done.

After elution, a sugar mixture solution (250 ml) of D-glucose, D-mannose, D-fructose, D-allose and D-psicose was obtained, with almost no browning change observed.

EXAMPLE 10

<Reaction of D-Tagatose with Strongly Basic Ion Exchange Resin>

With 0.1 mol/l NaOH solution, D-tagatose was adjusted to 10 w/v %. The resulting D-tagatose solution was passed through 38.5 ml of a packed strongly basic ion exchange resin at a temperature of 60° C. and a flow rate of 1.6 ml/min. (The resin: Amberlite IRA900J[Cl]; inner diameter: 1.5 cm). After the reaction solution eluted from the column was sampled over time, HPLC analysis (detector: RI; column: MCI GEL CK 08EC manufactured by Mitsubishi Kasei) was done.

After elution, a sugar mixture solution (250 ml) of D-galactose, D-tagatose, D-sorbose, D-idose and D-gulose was obtained, with almost no browning change observed. This clearly indicates that sugars in the block B were obtained from a sugar in the block B as the starting material by the process using the ion exchange resin.

EXAMPLE 11

<Reaction of L-Fructose with Strongly Basic Ion Exchange Resin>

With 0.1 mol/l NaOH solution, L-fructose was adjusted to 10 w/v %. The resulting L-fructose solution was passed through 38.5 ml of a packed strongly basic ion exchange resin at a temperature of 60° C. and a flow rate of 1.6 ml/min. (The resin: Amberlite IRA900J[Cl]; inner diameter: 1.5 cm). After the reaction solution eluted from the column was sampled over time, HPLC analysis (detector: RI; column: MCI GEL CK 08EC manufactured by Mitsubishi Kasei) was done.

After elution, a sugar mixture solution (250 ml) of L-glucose, L-mannose, L-fructose, L-allose, and L-psicose was obtained, with almost no browning change observed. This clearly indicates that sugars in the block D were obtained from a sugar in the block D as the starting material by the process using the ion exchange resin.

EXAMPLE 12

<Reaction of L-Tagatose with Strongly Basic Ion Exchange Resin>

With 0.1 mol/l NaOH solution, L-tagatose was adjusted to 10 w/v %. The resulting L-tagatose solution was passed through 38.5 ml of a packed strongly basic ion exchange resin at a temperature of 60° C. and a flow rate of 1.6 ml/min. (The resin: AmberliteIRA900J[Cl]; inner diameter: 1.5 cm). After the reaction solution eluted from the column was sampled over time, HPLC analysis (detector: RI; column: MCI GEL CK 08EC manufactured by Mitsubishi Kasei) was done.

After elution, a sugar mixture solution (250 ml) of L-galactose, L-tagatose, L-sorbose, L-idose and L-gulose was obtained, with almost no browning change observed. This clearly indicates that sugars in the block C were obtained from a sugar in the block C as the starting material by the process using the ion exchange resin.

EXAMPLE 13

<Continuous Reaction of Isomerized Sugar with Strongly Basic Ion Exchange Resin>

500 ml of 20% isomerized sugar solution was diluted to 10%, and was then passed through 38.5 ml of a packed strongly basic ion exchange resin at a temperature of 60° C. and a flow rate of 1.6 ml/min. (The resin: Amberlite IRA900J [Cl]; inner diameter: 1.5 cm). After the reaction solution (composition 1) was passed through a cation exchange resin column and a mix resin column, the eluate was decolored with active charcoal and filtered. The filtrate was concentrated. By separating the concentrated solution by simulated moving bed chromatography to isolate D-psicose, the isomerized sugar of an amount corresponding to the decreased amount was added to the separated solution of other sugar mixtures, which was then subjected to a basic ion exchange resin to obtain a reaction composition (composition 2). The composition was verified by HPLC described above.

The constitution ratios of the starting sugar material composition 1 and the starting sugar material composition 2 were almost identical. This apparently indicates that even the isomerized sugar mixed with the separated solution for reaction produced a reaction solution of a given constitution. The finding of the constitution indicates a possibility of continuous separation.

EXAMPLE 14

<Sensory Test of Sugar Solution Produced on Strongly Basic Ion Exchange Resin>

Six panelists were enrolled in a taste test of the 10% sugar solution prepared in Example 7. By selecting the quality of the sweetness from ranks at the same sweetness as that of sugar, "light", "identical" and "heavy" compared with the sweetness of sugar, evaluation was done. Counting the number of persons carrying out the selection, a sensory test was executed. The panelists were six males and females with refined taste in the years of 20's to 30's.

Consequently, the taste of the mix solution of sugars as obtained by the process was like sugar.

EXAMPLE 15

<Production of Acidic Drink containing Sugar Solution Produced on Strongly Basic Ion Exchange Resin>

A drink was prepared by the process using a sugar mixture and sucrose. The taste of the drink using the sugar mixture solution obtained by the process was like sugar.

EXAMPLE 16

<Reaction 1 with no Use of Resin>

With 0.1 mol/l NaOH solution, D-fructose was adjusted to 10 w/v % and heated at 60° C. The resulting D-fructose solution was sampled at a 13-min heating time and a 20-min heating time. To the individual sampled sugar solutions was added a strongly acidic ion exchange resin (Amberlite 200CT [H form]), for neutralization. The constitutions of the individual sugar solutions were analyzed by HPLC (detector: RI; column: MCI GEL CK 08EC manufactured by Mitsubishi Kasei)

The sugar constitution of the reaction solution after 13-min heating was D-glucose at 16.4%, (D-mannose+D-sorbose+D-altrose) at 4.7%, D-fructose at 70.9%, D-allose at 0.9% and D-psicose at 4.7% of the sugar content, while the coloring level was 0.37 (on a BRIX10 basis). Further, the sugar constitution of the reaction solution after 20-min heating was D-glucose at 21.9%, (D-mannose+D-sorbose+D-altrose) at 7.0%, D-fructose at 60.1%, D-allose at 1.5% and D-psicose at 6.3%, while the coloring level was 0.87 (on a BRIX10 basis). Compared with the sugar solutions obtained in Examples 1 and 2, the coloring levels thereof were 10 to 30 fold. This apparently indicates that the process using such resins is excellent in terms of subsequent purification efficiency, although the inventive composition can be obtained by the processes with no use of resin. Herein, it is noted that sorbose is a byproduct through reverse aldol condensation and its yield may be about several %.

EXAMPLE 17

<Reaction 2 with no Use of Resin>

With 0.07 mol/l $Ca(OH)_2$ solution, an isomerized sugar (D-glucose at 55 w/w %, D-fructose at 45 w/w %) was adjusted to 10 w/v %, for reaction at 60° C. for one hour. The sugar solution after the reaction was desalted, and its sugar constitution was analyzed by HPLC (detector: RI; column: MCI GEL CK 08EC manufactured by Mitsubishi Kasei).

The sugar constitution of the reaction solution was D-glucose at 39.8%, (D-mannose+D-sorbose+D-altrose) at 10.8%, D-fructose at 27.8%, D-allose at 2.8% and D-psicose at 5.2% of the sugar content. It apparently indicates that the inventive composition can be obtained with not only sodium hydroxide but also calcium hydroxide. Using 0.0029 mol/l $Ca(OH)_2$ solution, an experiment was done under the same conditions. A composition containing D-psicose at 1.3% and D-allose at 0.3% was obtained in a 2-hour reaction.

EXAMPLE 18

<Reaction 3 with no Use of Resin>

Under the conditions in Example 4, namely under conditions with no use of any resin, a reaction of D-fructose in 0.1 mol/l NaOH solution in a heated cell was done.

With 0.1 mol/l NaOH solution, D-fructose was adjusted to 10 w/v %. The resulting D-fructose solution of 600 ml was passed through a heated cell at 60° C. (length: 30 cm; inner diameter: 1.5 cm) and 26 ml of a strongly acidic ion exchange resin in this order, at a flow rate of 1.6 ml/min. (The strongly acidic ion exchange resin: Amberlite 200CT [H form]). The reaction solution eluted from the heated cell was sampled over time, for HPLC analysis (detector: RI; column: MCI GEL CK 08EC manufactured by Mitsubishi Kasei).

The sugar constitution of the solution (600 ml) after elution was D-glucose at 18.2%, (D-mannose+D-sorbose+D-altrose) at 5.9%, D-fructose at 67.0%, D-allose at 1.2% and D-psicose at 5.1% of the sugar content, while the coloring level was 1.24. This apparently indicates that the reaction progresses by heating alone but the reaction speed was large in case that the strongly basic ion exchange resin in Example 4 was used, together with the low coloring level, so that the use of the strongly basic ion exchange resin was advantageous in terms of production efficiency.

EXAMPLE 19

<Reaction of D-Glucose with Strongly Basic Ion Exchange Resin>

With 0.1 mol/l NaOH solution, D-glucose was adjusted to 10 w/v %. The resulting D-glucose solution was passed through 45 ml of a strongly basic ion exchange resin (resin: Amberlite IRA900J OH; column length: 30 cm; inner diameter: 1.5 cm) and 26 ml of a strongly acidic ion exchange resin (resin: Amberlite IRA200CT [H form]; column length: 30 cm; inner diameter: 1.5 cm) in this order, at a temperature of 60° C. and a flow rate of 1.6 ml/l. After the reaction solution eluted from the column was sampled over time, the samples were analyzed by HPLC (detector: RI; column: MCI GEL CK 08EC manufactured by Mitsubishi Kasei).

After elution, a sugar mixture solution (400 ml) of D-glucose at 47.4 (D-mannose+D-sorbose+D-altrose) at 9.6%, D-fructose at 32.1%, D-allose at 2.7% and D-psicose at 5.7% of the sugar content was obtained, with almost no browning observed. This clearly indicates that sugars (ketose and aldose) in the block A can be obtained, using D-glucose (aldose) as the starting material.

EXAMPLE 20

<Reaction of D-Fructose in 0.005 mol/l NaOH Solution with Strongly Basic Ion Exchange Resin>

With 0.005 mol/l NaOH solution, D-fructose was adjusted to 10 w/v %. The resulting D-fructose solution of 1100 ml was passed through 45 ml of a strongly basic ion exchange resin and 26 ml a strongly acidic ion exchange resin in this order, at a temperature of 60° C. and a flow rate of 0.8 ml/min (The strongly basic ion exchange resin: Amberlite IRA900J OH; column length: 30 cm; inner diameter: 1.5 cm). After the reaction solution eluted from the column was sampled over time, the samples were analyzed by HPLC (detector: RI; column: MCI GEL CK 08EC manufactured by Mitsubishi Kasei).

After elution, a sugar mixture solution (1000 ml) of D-glucose at 9.4%, (D-mannose+D-sorbose+D-altrose) at 3.2 D-fructose at 80.0%, D-allose at 1.1% and D-psicose at 3.9% of the sugar content was obtained. Under the same conditions except for no NaOH addition, the solution was passed through the column. A sugar mixture solution of D-glucose at 6.2%, (D-mannose+D-sorbose+D-altrose) at 2.3%, D-fructose at 86.1%, D-allose at 0.9% and D-psicose at 2.9% of the sugar content was obtained. Apparently, the process using the alkali solution as a starting material is effective as a process of improving the productivity of an target sugar hexose via the suppression of the reduction of the reaction efficiency. As to the alkali concentration, the reaction progresses more as the amount of the charged alkali increases. Even at a slight amount, the inventive composition can be obtained by increasing or raising the reaction time and the temperature. So as to obtain the inventive composition highly efficiently in a short time of about one hour or at a low temperature of about 60° C., a solution of an alkali concentration of 0.005 mol/l or more is preferable.

EXAMPLE 21

<Reaction of Isomerized Sugar Syrup in 0.1 mol/l NaOH Solution with Strongly Basic Ion Exchange Resin>

With 0.1 mol/l NaOH solution, an isomerized sugar syurup was adjusted to 10 w/v %. The resulting solution of 500 ml was passed through 45 ml of a strongly basic ion exchange resin and 26 ml a strongly acidic ion exchange resin in this order, at a temperature of 60° C. and a flow rate of 1.6 ml/min. [The strongly basic ion exchange resin: Amberlite IRA900J OH; strongly acidic ion exchange resin: Amberlite 200CT [H form]; column length: 30 cm; inner diameter: 1.5 cm]. After the reaction solution eluted from the column was sampled over time, the samples were analyzed by HPLC (detector: RI; column: MCI GEL CK 08EC manufactured by Mitsubishi Kasei).

Figure 7:
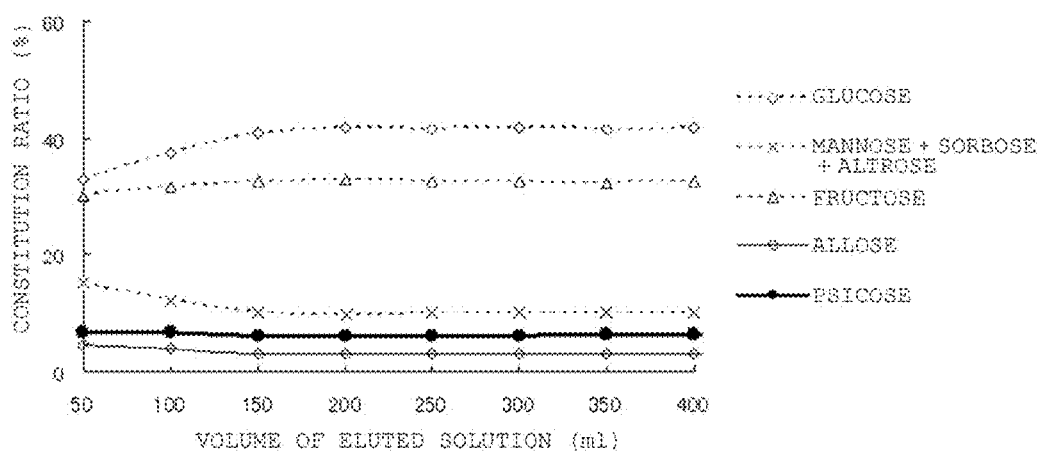
FIG. 7 Graphs depicting the analyzed composition of a sugar mixture containing the target sugar in Example 21 entitled <Reaction of isomerized sugar syrup in 0.1 mol/l NaOH solution with strongly basic ion exchange resin>.

The analyzed composition is shown in FIG. 7. The sugar constitution of the solution (400 ml) after elution was D-glucose at 40.3%, (D-mannose+D-sorbose+D-altrose) at 10.7%, D-fructose at 32.2%, D-allose at 3.2% and D-psicose at 6.3% of the sugar content. As in Example 2, the process comprising passing an alkali solution together with a raw material through a column never decreases the reaction efficiency even when an isomerized sugar syrup was used as a starting material. This indicates that the process is effective as a process of improving the productivity of an target hexose by passing the alkali solution through the column to suppress adsorption of the starting sugar material and byproducts onto the resins.

EXAMPLE 22

<Reaction of 5% Isomerized Sugar Syrup with Strongly Basic Ion Exchange Resin>

With 0.1 mol/l NaOH solution, an isomerized sugar syrup was adjusted to 5 w/v %. The resulting solution of 1100 ml was passed through 45 ml of a strongly basic ion exchange resin and 26 ml a strongly acidic ion exchange resin in this order, at a temperature of 60° C. and a flow rate of 0.8 ml/min. [The strongly basic ion exchange resin: Amberlite IRA900J OH; strongly acidic ion exchange resin: Amberlite 200CT [H form]; column length: 30 cm; inner diameter: 1.5 cm]. After the reaction solution eluted from the column was sampled over time, the samples were analyzed by HPLC (detector: RI; column: MCI GEL CK 08EC manufactured by Mitsubishi Kasei).

After elution, a sugar mixture solution (1000 ml) of D-glucose at 34.3 (D-mannose+D-sorbose+D-altrose) at 12.4%, D-fructose at 25.8%, D-allose at 4.1% and D-psicose at 6.3% of the sugar content was obtained. The inventive composition can be obtained by using a starting sugar material in the block A even in a diluted solution to obtain sugars in the block A. So as to simplify subsequent concentration, particularly, a raw material solution of about 5% or more is preferable.

EXAMPLE 23

<Reaction of 40% Isomerized Sugar Syrup with Strongly Basic Ion Exchange Resin>

With 0.1 mol/l NaOH solution, an isomerized sugar syrup was adjusted to 40 w/v %. The resulting solution of 1100 ml was passed through 45 ml of a strongly basic ion exchange resin and 26 ml a strongly acidic ion exchange resin in this order, at a temperature of 60° C. and a flow rate of 0.8 ml/min. [The strongly basic ion exchange resin: Amberlite IRA900J OH; strongly acidic ion exchange resin: Amberlite 200CT [H form]; column length: 30 cm; inner diameter: 1.5 cm]. After the reaction solution eluted from the column was sampled over time, the samples were analyzed by HPLC (detector: RI; column: MCI GEL CK 08EC manufactured by Mitsubishi Kasei).

After elution, a sugar mixture solution (1000 ml) of D-glucose at 46.2%, (D-mannose+D-sorbose+D-altrose) at 6.3%, D-fructose at 32.8%, D-allose at 2.0% and D-psicose at 4.8% of the sugar content was obtained. Because the yield of the produced rare sugar hexose is small compared with the yields in Examples 21 and 22, it is indicated that the yield of rare sugar hexose can be raised as the concentration of a starting liquid sugar material is lower. This apparently indicates that in view of the production efficiency, the concentration of a starting liquid sugar material is 5% to 40%, preferably about 10 to 30%, in particular.

EXAMPLE 24

<Reaction of D-Tagatose with Strongly Basic Ion Exchange Resin>

With 0.1 mol/l NaOH solution, a sugar solution containing D-tagatose as the main component (at 90% or more) is adjusted to 10 w/v %. The resulting solution of 500 ml was passed through 45 ml of a strongly basic ion exchange resin and 26 ml a strongly acidic ion exchange resin in this order, at a temperature of 60° C. and a flow rate of 1.6 ml/min. [The strongly basic ion exchange resin: Amberlite IRA900J OH; strongly acidic ion exchange resin: Amberlite 200CT [H form]; column length: 30 cm; inner diameter: 1.5 cm]. After the reaction solution eluted from the column was sampled over time, the samples were analyzed by HPLC (detector: RI; column: MCI GEL CK 08EC manufactured by Mitsubishi Kasei). Further, the taste of a 30-% solution of the resulting sugar solution was examined.

After elution, a sugar mixture solution (400 ml) of D-glucose at 1.8%, (D-galactose+D-sorbose) at 45.1%, D-idose at 8.7%, (D-tagatose+D-gulose) at 29.2%, and D-talose at 8.8% of the sugar content was obtained. This indicates that sugars in the block B can be produced from a starting sugar material in the block B by the process using ion exchange resins. Additionally, the taste of the sugar mixture was like sugar.

EXAMPLE 25

<Reaction of L-Sorbose with Strongly Basic Ion Exchange Resin>

With 0.1 mol/l NaOH solution, L-sorbose is adjusted to 10 w/v %. The resulting solution of 500 ml was passed through 95 ml of a strongly basic ion exchange resin and 26 ml a strongly acidic ion exchange resin in this order, at a temperature of 60° C. and a flow rate of 1.6 ml/min. [The strongly basic ion exchange resin: Amberlite IRA900J OH; strongly acidic ion exchange resin: Amberlite 200CT [H form]; column length: 30 cm; inner diameter: 1.5 cm]. After the reaction solution eluted from the column was sampled over time, the samples were analyzed by HPLC (detector: RI; column: MCI GEL CK 08EC manufactured by Mitsubishi Kasei). Further, the taste of a 30-% solution of the resulting sugar solution was examined.

After elution, a sugar mixture solution (400 ml) of L-glucose at 2.0%, (L-galactose+L-sorbose) at 59.2%, L-idose at 9.9%, (L-tagatose+L-gulose) at 17.2%, and L-talose at 5.0% of the sugar content was obtained. This indicates that sugars in the block C can be produced from a starting sugar material in the block C by the process using ion exchange resins. Additionally, the taste of the sugar mixture was like sugar.

EXAMPLE 26

<Reaction of L-Psicose with Strongly Basic Ion Exchange Resin>

With 0.1 mol/l NaOH solution, L-psicose is adjusted to 10 w/v %. The resulting solution of 500 ml was passed through 45 ml of a strongly basic ion exchange resin and 26 ml a strongly acidic ion exchange resin in this order, at a temperature of 60° C. and a flow rate of 1.6 ml/min. [The strongly basic ion exchange resin: Amberlite IRA900J OH; strongly acidic ion exchange resin: Amberlite 200CT [H form]; column length: 30 cm; inner diameter: 1.5 cm]. After the reaction solution eluted from the column was sampled over time, the samples were analyzed by HPLC (detector: RI; column: MCI GEL CK 08EC manufactured by Mitsubishi Kasei). Further, the taste of a 30-% solution of the resulting sugar solution was examined.

After elution, a sugar mixture solution (400 ml) of L-glucose at 7.7%, (L-sorbose+L-mannose+L-altrose) at 17.7%, L-fructose at 21.5%, L-allose at 12.4%, and L-psicose at 34.1% of the sugar content was obtained. This indicates that sugars in the block D can be produced from a starting sugar material in the block D by the process using the ion exchange resins. Additionally, the taste of the sugar mixture was like sugar.

EXAMPLE 27

<Continuous Reaction of Isomerized Sugar Syrup with Strongly Basic Ion Exchange Resin>

With 0.1 mol/l NaOH solution, an isomerized sugar syrup is adjusted to 10 w/v %. The resulting solution was passed through a strongly basic ion exchange resin and a strongly acidic ion exchange resin in this order, at a temperature of 60° C. [The strongly basic ion exchange resin: Amberlite IRA900J OH; strongly acidic ion exchange resin: Amberlite 200CT [H form]]. After the reaction solution (composition 1) was purified, only D-psicose was separated by simulated moving bed chromatography, while the remaining sugar solution was subjected to the basic ion exchange resin under the conditions described above, to obtain a reaction composition (composition 2). The compositions were verified by HPLC described above.

The composition 1 was at D-glucose at 40.1%, (D-mannose+D-sorbose+D-altrose) at 11.4%, D-fructose at 32.5%, D-allose at 3.4%, and D-psicose at 6.7% of the sugar content. The composition 2 was at D-glucose at 33.2%, (D-mannose+D-sorbose+D-altrose) at 16.1%, D-fructose at 14.3%, D-allose at 4.6%, and D-psicose at 6.1% of the sugar content. This apparently indicates that the target sugar hexose can singly be obtained by separating the target sugar hexose from the reaction products, and using the remaining solution again as a starting sugar material for reaction and separation. As described above, the reaction and separation steps are repeatedly carried out, to efficiently obtain the target sugar hexose.

EXAMPLE 28

<Hexose Reaction using Calcium>

4.0 g of calcium chloride and 0.25 g of D-fructose were added to 6.0 g of water, for reaction at 60° C. for 30 minutes. After the reaction solution was sampled, the samples were analyzed by HPLC (detector: RI; column: MCI GEL CK 08EC manufactured by Mitsubishi Kasei).

As the consequence of the analysis, a sugar mixture solution of D-glucose at 2.54%, (D-mannose+D-sorbose+D-altrose) at 4.0913, D-fructose at 86.54%, D-allose at 0.72%, and D-psicose at 4.82% of the sugar content was obtained. This indicates that the inventive composition was obtained by using the catalytic reaction of calcium as well.

EXAMPLE 29

<Assaying D-Psicose contained in Isomerized Sugar Syrup>

Since the content of D-psicose in isomerized sugar syrup is very low, it was difficult to assay D-psicose by the previous methods. D-psicose was assayed by HPLC, after assimilating isomerized sugar syrup with yeast to remove glucose and fructose as the main sugars.

11.5 g of dry yeast was suspended in 100 ml of a sodium alginate solution at a concentration of 2%. By dropwise adding the suspension into a sufficiently cooled calcium chloride solution at a 5-% concentration, an immobilized gel containing yeast was prepared. 14.4 g of an isomerized sugar syrup (Fujifract 95, Nippon Shokuhin Kako Co., Ltd.) and 85.6 g of pure water were charged to a final volume of 100 ml in an Erlenmeyer flask. The solution contains the isomerized sugar syrup of 10 g as the solid content. The solution, an inner standard and the immobilized yeast measured up to a position corresponding to 50 ml in a measuring cylinder were placed together in a 500-ml Erlenmeyer flask, for shaking culture with a shaking culture unit for 24 hours. After completion of culture, yeast was removed through a 0.8-μm cellulose film filter (manufactured by Advantec), while desalting was done by passing the solution through an ion exchange resin; then, the resulting solution was concentrated with a rotary evaporator, for analysis by HPLC (detector: RI; column: MCI GEL CK 08EC manufactured by Mitsubishi Kasei).

The content of D-psicose in the isomerized sugar syrup was 0.1%. This apparently indicates that D-psicose was contained in the isomerized sugar syrup. This reveals that the production process of D-psicose by the ion exchange resin process in this Example is a process of further greatly raising the content of D-psicose contained in the isomerized sugar syrup.

EXAMPLE 30

<Production Efficiency of D-Psicose Depending on the Resin Type>

Using four types of ion exchange resins (IRA400J, IRA900J, IRA900J[Cl], IRA904), a resin with a high isomerization efficiency was examined. An isomerized sugar syrup adjusted to 10 w/v % with 0.1 mol/l NaOH solution was passed through a column packed with 2 liters of a basic ion exchange resin at a temperature of 60° C. and a flow rate of 2 l/h.

After the reaction solution was sampled over time, HPLC (detector: RI; column: GL-C611 manufactured by Hitachi High Technologies) analysis was done.

Figure 8:
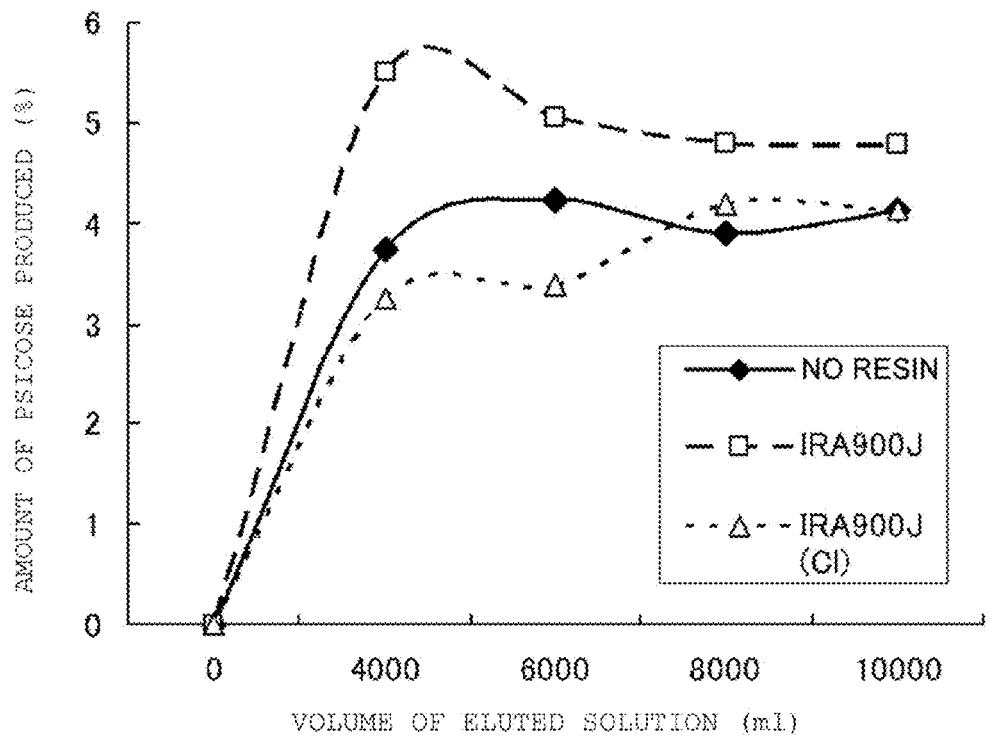
FIG. 8 Graphs depicting the high reaction efficiency when the resin is used in Example 30 entitled <Production efficiency of D-psicose depending on the resin type> and that the efficiency is higher with the OH type than with the Cl type.
Figure 9:
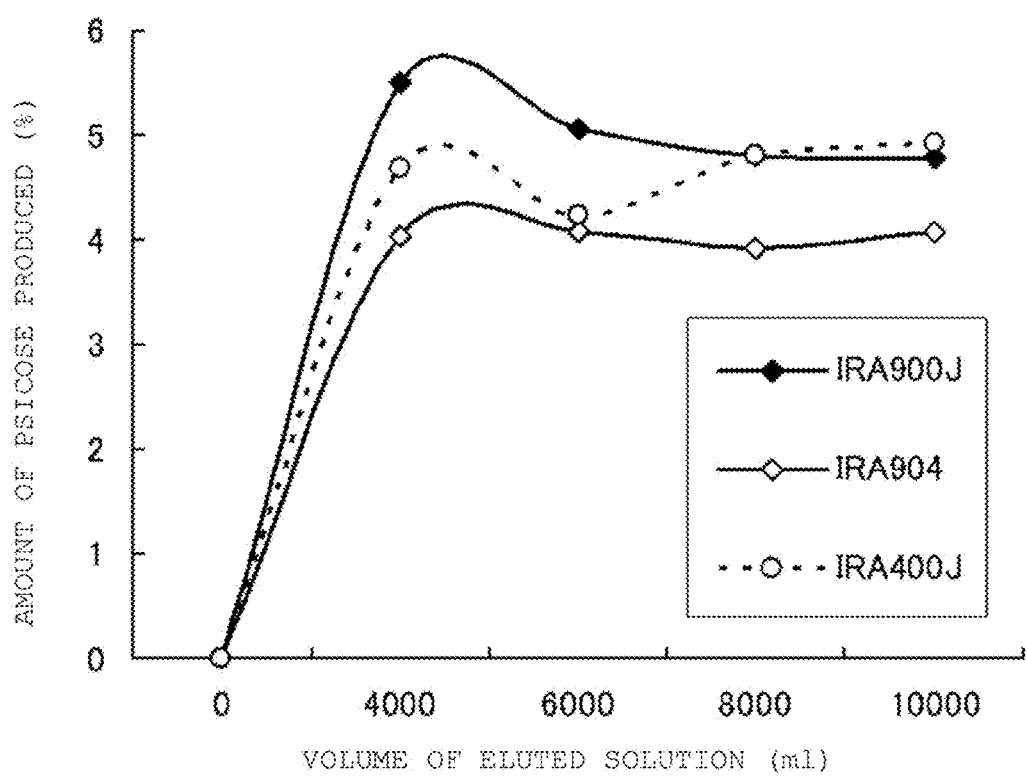
FIG. 9 Graphs depicting that the reaction efficiency is higher with the porous form of the mother resin in Example 30 entitled <Production efficiency of D-psicose depending on the resin type> than with the gel form thereof and that the reaction efficiency is higher when the total exchange volume is large than when the total exchange volume is small.

As shown in FIGS. 8 and 9, the isomerization efficiency depending on the resin type was examined. The results in FIG. 8 show that the reaction efficiency was higher when the resin was used than when no resin was used; and that the efficiency was higher with the OH type (IRA900J) than with the Cl type (IRA900J [Cl]). The results in FIG. 9 show that the reaction efficiency was higher with the mother resin of the porous form (IRA900J) than with the mother resin of the gel form (IRA400J) and that the reaction efficiency was higher when the total ion exchange volume was large (IRA900J: ≥1.0 mg equivalent/ml wet resin) than when the total ion exchange volume was small (IRA904: ≥0.65 mg equivalent/ml wet resin).

EXAMPLE 31

(Sensory Test of Sugar Solution Comprising D-Psicose and D-Allose)

A taste test of 10 w/v % sugar solutions (1-8) of the constitutions in Table 1 was done by six male and female panelists in the years of 20's to 50's with refined taste. Regarding sweetness level, good aftertaste, sharp sweetness, balanced sweetness, and texture, evaluation was done. The panelists voted sugar solutions (1-8) that were designated as greatest. Additionally, the taste was evaluated by a questionnaire survey on comparison with that of sucrose. Further, the sugar solution 7 and the composition produced in Example 21 (containing D-glucose at 40.3%, D-fructose at 32.2%, D-allose at 3.2%, D-psicose at 6.3%, and (D-mannose+D-sorbose+D-altrose) at 10.7) were compared with each other regarding the taste.

TABLE 1

Results of sensory test of sugar solutions

| | Glucose | Mannose | Sorbose | Fructose | Psicose | Allose | Sweetness level | Aftertaste length | Sharp sweetness | Balance of sweetness | Texture | Total |
|---|---|---|---|---|---|---|---|---|---|---|---|---|
| 1 | 58 | 0 | 0 | 42 | 0 | 0 | 1 | | 1 | | | 2 |
| 2 | 45 | 0 | 0 | 55 | 0 | 0 | 2 | | 1 | | | 3 |
| 3 | 56 | 7.5 | 4.5 | 32 | 0 | 0 | | 2 | | | | 2 |
| 4 | 49.5 | 7.5 | 4.5 | 32 | 6.5 | 0 | 1 | 1 | | | 1 | 3 |
| 5 | 52.5 | 7.5 | 4.5 | 32 | 0 | 3.5 | 1 | 1 | 1 | | | 3 |
| 6 | 54.6 | 7.5 | 4.5 | 32 | 1 | 0.4 | 1 | | 1 | 2 | 1 | 5 |
| 7 | 46 | 7.5 | 4.5 | 32 | 6.5 | 3.5 | | 1 | 1 | 3 | 2 | 7 |
| 8 | 33 | 7.5 | 4.5 | 32 | 15 | 8 | | 1 | 1 | 1 | 2 | 5 |

The results in Table 1 apparently show that the compositions (sugar solutions 6, 7, 8) comprising D-psicose and D-allose got improved taste compared with the existing isomerized sugar syrup (sugar solutions 1, 2). Particularly, the sugar solutions of the invention (sugar solutions 6, 7, 8) were excellent in terms of balance of sweetness and texture and even when the content thereof was low or even when the content thereof was high, the effect on the taste improvement was observed. Furthermore, the taste of the sugar solution 7 and that of the sugar solution obtained in Example 21 were compared with each other. Almost no difference in their tastes was observed. Regarding the individual compositions (sugar solutions 1 to 8) and a 10-% sucrose solution, the tastes thereof were compared with each other. Consequently, the compositions comprising D-psicose and D-allose showed a taste close to the taste of sugar, compared with the remaining compositions. Because the sweetness level of D-allose is about 0.8 fold that of sucrose and the taste thereof is close to that of sugar, D-allose may exert an effect of improving sweetness. The compatibility of D-allose with D-psicose in particular would possibly be high.

EXAMPLE 32

<Production of Acidic Drink Containing Sugar Solution comprising D-Psicose and D-Allose>

At the ratios shown in Table 2, drinks were prepared using the sweetener of the invention (the sugar solution obtained by the process in Example 21) and sucrose.

TABLE 2

Table of blending ratios of sugar solutions

| | Blending ratios | | | | |
|---|---|---|---|---|---|
| | a | b | c | d | e |
| Glucose | 4.6 | 5.46 | 3.3 | | |
| Mannose | 0.75 | 0.75 | 0.75 | | |
| Sorbose | 0.45 | 0.45 | 0.45 | | |
| Fructose | 3.2 | 3.2 | 3.2 | | |
| Psicose | 0.65 | 0.1 | 1.5 | | |
| Allose | 0.35 | 0.04 | 0.8 | | |
| Sweetener of the Example | | | | 10 | |
| Sucrose | | | | | 10 |
| Citric acid | 0.1 | 0.1 | 0.1 | 0.1 | 0.1 |
| Flavor | 0.1 | 0.1 | 0.1 | 0.1 | 0.1 |
| Carbonic acid | 50 | 50 | 50 | 50 | 50 |
| Water | to 100 | to 100 | to 100 | to 100 | to 100 |

Drinks were prepared, using sugar solutions comprising D-psicose and D-allose (at the blending ratios of a, b and c), the sugar solution obtained in Example 21 (at the blending ratio of d) and sucrose (at the blending ratio of e). Consequently, all the sugar solutions at the blending ratios of a, b, c and d compared with the sucrose solution at the blending ratio of e had a sugar-like taste. This indicates that the composition of the patent comprising D-psicose and D-allose can be used as a sucrose-like sweetener.

EXAMPLE 33

<Physiological Effects of Sugar Solutions comprising D-Psicose and D-Allose>

By isomerizing an existing isomerized sugar syrup at blending ratios having been known, in accordance with the invention, glucose and fructose as sugars composing the isomerized sugar syrup are isomerized to obtain a composition containing D-psicose at about 7% and D-allose at about 4% (referred to as inventive composition hereinafter). Compared with an existing isomerized sugar syrup (glucose at 55% and fructose at 45%), the function of the composition obtained by the inventive process was examined in rats.

[Experimental Method]

As experimental animals, male Wistar rats of age three weeks were used. An isomerized sugar intake group (sugar material derived from isomerized sugar syrup at 28.5%+ starch at 28.5% (w/w)), an inventive composition intake group fed by the inventive composition in place of the isomerized sugar syrup (sugar material derived from the inventive composition at 28.5%+starch at 28.5% (w/w)), and a starch intake group (starch at 57%) as a control group were prepared. Casein at 17.5% as a protein source and powder oils and fats at 43.9% as a lipid source were used in the feed. The experimental feeds and water were fed ad libitum for feeding for 8 weeks.

After the termination of the feeding, body weight was measured followed by autopsy. At the autopsy, blood was collected for assaying blood sugar level and insulin level. By collecting body fat, the weight thereof was measured. Feed intake was counted in total. The assay or measured values were expressed as mean and standard deviation, for multiple testing.

Herein, the sugar material derived from isomerized sugar syrup in the isomerized sugar intake group (A) contains D-glucose at 55% and D-fructose at 45%; as the sugar material derived from the inventive composition in the inventive composition intake group (B), the composition obtained by the process in Example 21 was used, which contained D-glucose at 40%, O-fructose at 31%, (D-mannose+D-sorbose+D-altrose) at 12%, D-psicose at 7% and D-allose at 4%.

[Results]

Body weight increment was 195±21 in the starch (control group), 189±15 in the isomerized sugar group, and 158±17 in the inventive composition group; compared with the control group and the isomerized sugar group, significant reduction of body weight was observed in the inventive composition group ($p<0.01$). Epididymis fat tissue weight (g) was 7.85±1.7 in the starch (control group), 8.56±1.4 in the isomerized sugar group, and 4.62±0.7 in the inventive composition group; compared with the control group and the isomerized sugar group, significant reduction of the fat tissue weight was observed in the inventive composition group ($p<0.01$). Perinephrium fat weight (g) was 7.05±1.1 in the starch (control group), 7.84±1.4 in the isomerized sugar group, and 4.74±0.8 in the inventive composition group; compared with the control group and the isomerized sugar group, significant reduction of the fat tissue was observed in the inventive composition group ($p<0.01$). Mesenterium fat tissue weight (g) was 5.34±1.2 in the starch (control group), 6.30±1.3 in the isomerized sugar group, and 3.76±0.6 in the inventive composition group; compared with the control group and the isomerized sugar group, significant reduction of the fat tissue weight was observed in the inventive composition group ($p<0.01$). Total fat tissue weight (g) in abdominal cavity was 20.2±3.8 in the starch (control group), 22.7±3.9 in the isomerized sugar group and 13.1±1.9 in the inventive composition group; compared with the control group and the isomerized sugar group, significant reduction of fat tissue weight was observed in the inventive composition group ($p<0.01$).

Additionally, the amount of feed intake (g/day) was 18.1±1.8 in the starch (control group), 18.6±1.9 in the isomerized sugar group, and 16.6±1.5 in the inventive composition group; compared with the control group and the isomerized sugar group, significant reduction of feed intake was observed in the inventive composition group ($p<0.05$, $p<0.01$).

The body weight decrement, the body fat decrement and the reduction of the amount of feed intake due to D-psicose or D-allose are reported in the non-patent reference 8 (report 1) and the non-patent reference 9 (report 2); according to the reports, the body weight decrement, the body fat decrement and the reduction of feed intake (%) in the D-psicose or D-allose intake group compared with the body weight decrement, the body fat decrement and the reduction of feed intake in the control group are as follows. Non-patent reference 10 (report 4) describes that the D-mannose contained in the inventive composition never makes any contribution to body weight and the amount of feed intake.

Comparison of the results (Table 3) shows apparently that the composition containing D-psicose and D-allose at the experiment synergistically exhibits a body weight decrement ratio, a body fat decrement ratio and a feed intake decrement ratio, on comparison of the contents thereof. Furthermore, the values in the report 1 and the report 2 are individually values calculated on a basis of D-psicose at 2.3% or on a basis of D-allose at 1.3%. This indicates that the inventive composition containing D-psicose and D-allose is a composition with a body fat decrement ratio and a feed intake decrement ratio, which has never been observed so far. At the experiment, additionally, the blood sugar level in the starch (control) group was 115±17; the blood sugar level in the isomerized sugar group was 95±12; and the blood sugar level in the inventive composition group was 98±21. Compared with the control group, significant reduction was observed in the inventive composition group (p<0.05). Compared with the isomerized sugar group, no significant difference was observed therein. The insulin level (ng/dl) in the starch (control) group was 3.2±0.9; and the insulin level in the isomerized sugar group was 3.7±1.1; and the insulin level in the inventive composition group was 2.3±0.9. Compared with the control group and the isomerized sugar group, significant reduction of body weight was observed in the inventive composition group (p<0.05, p<0.01). No significant reduction of blood sugar level and insulin level was observed with D-psicose and D-allose in the reports 1 and 2. Regarding the intra-day variation of insulin level in case of D-psicose administration, no reduction of insulin level was reported (see non-patent reference 11). This apparently indicates that the composition has an effect of ameliorating sugar metabolism, particularly an effect of ameliorating insulin resistance.

TABLE 3

Body weight decrement ratio, body fat decrement ratio, and feed intake decrement ratio

|  | Report 1 | Report 2 | Report 1 + Report 2 | Experiment |
|---|---|---|---|---|
| D-psicose or D-allose content (%) in total solids | D-psicose at 5% | D-allose at 3% | D-psicose at 2.3% + D-allose at 1.3% | D-psicose at 2.3% + D-allose at 1.3% |
| Body weight decrement ratio (%) | 6 | 17 | 10 | 16 |
| Body fat decrement ratio (%) | 15 | 19 | 15 | 42 |
| Feed intake decrement ratio (%) | 6 | 8 | 6 | 11 |

INDUSTRIAL APPLICABILITY

It is expected that the hexose composition containing rare sugars such as D-psicose and D-allose in accordance with the invention can be used widely as a sweetener for not only soft drinks and other drinks but also foods, pharmaceutical products, oral compositions and cosmetics. The hexose composition produced by using an isomerized sugar syrup as a starting sugar material in accordance with the invention can be produced and provided at a large scale and at a low production cost. It is also expected that the range of the use of the hexose composition can be enlarged by utilizing the excellent characteristic properties thereof.

The invention claimed is:

1. A process of producing a sugar composition comprising a definite amount of a target hexose, wherein the target hexose comprises D-psicose in a range of 5 to 10 wt % and D-allose in a range 1.5 to 5 wt %, comprising:
   i) preparing a starting liquid sugar material as an alkaline solution at 0.005 to 0.1 M alkali, the staring liquid sugar material being an isomerized sugar syrup containing D-glucose and D-fructose as the main components, and then,
   ii) isomerizing the alkaline solution via treatment at a temperature between 40° C. and 70° C. in the presence of at least a basic ion exchange resin, and thus performing an isomerization reaction which is an equilibrium reaction for transforming the starting sugar material into the target hexose, wherein the concentration of the hexose in the starting liquid sugar material is 5.0 w/v % to 40.0 w/v %.

2. A process of producing a sugar composition according to claim 1, where the starting liquid sugar material is isomerized in the presence of a basic ion exchange resin, followed by passing the resulting solution through an acidic ion exchange resin and/or a mixed ion exchange resin for neutralizing and desalting.

3. A process of producing a sugar composition according to claim 1, where the target hexose is separated from the sugar mixture and the resulting residue is returned as a raw material to the starting liquid sugar material.

4. A process of producing a sugar composition according to claim 1, wherein said starting liquid sugar material is prepared as an alkaline solution at 0.1 M alkali.

5. A process of producing a sugar composition comprising a definite amount of a target hexose, wherein the target hexose comprises D-psicose at about 9.5 wt % and D-allose at about 10.0 wt %, comprising:
   treating a starting liquid sugar material which is an isomerized sugar syrup containing D-glucose and D-fructose as main components, at 100° C., in the presence of at least one member selected from the group consisting of an alkali and a calcium salt, while maintaining a pH of the liquid sugar material to at least 11 and thus performing an isomerization reaction which is an equilibrium reaction for transforming the starting sugar material into the target hexose, wherein the concentration of the hexose in the starting liquid sugar material is 5.0 w/v % to 40.0 w/v %.

6. A process of producing a sugar composition according to claim 5, where the concentration of the alkali in the starting liquid sugar material is 0.005 mol/l or more as the starting liquid sugar material is treated in the presence of the alkali.

7. A process of producing a sugar composition according to claim 5, where the concentration of the calcium salt in the starting liquid sugar material is 0.005 mol/l or more as the starting liquid sugar material is treated in the presence of the calcium salt.

8. A process of producing a sugar composition according to claim 5, where the target hexose is separated from the sugar mixture and the resulting residue is returned as a raw material to the starting liquid sugar material.

* * * * *